United States Patent [19]
Yoo et al.

[11] Patent Number: 6,025,387
[45] Date of Patent: Feb. 15, 2000

[54] GASTROPROTECTIVE FLAVONE/FLAVANONE COMPOUNDS WITH THERAPEUTIC EFFECT ON INFLAMMATORY BOWEL DISEASE

[75] Inventors: Moohi Yoo, Seoul; Mi Won Son; Ik Yon Kim, both of Kyoungki-do; Won Bae Kim, Seoul; Soon Hoe Kim, Kyoungki-do; Sang Deuk Lee, Seoul; Geun Jho Lim, Seoul; Joong In Lim, Seoul; Byoung Ok Ahn, Kyunggi-do; Nam Gi Baik; Dong Sung Kim, both of Kyoungki-do; Tae Young Oh, Kyunggi-do; Byung Kwon Ryu, Seoul; Jae Sung Yang, Seoul; Hee Chan Shin, Seoul, all of Rep. of Korea

[73] Assignee: Dong a Pharmaceutical Co., Ltd., Rep. of Korea

[21] Appl. No.: 09/214,889

[22] PCT Filed: Jul. 25, 1997

[86] PCT No.: PCT/KR97/00144

§ 371 Date: Jan. 14, 1999

§ 102(e) Date: Jan. 14, 1999

[87] PCT Pub. No.: WO98/04541

PCT Pub. Date: Feb. 5, 1998

[30] Foreign Application Priority Data

Jul. 25, 1996 [KR] Rep. of Korea ............ 96/30494

[51] Int. Cl.$^7$ ............ A61K 31/365; C07D 311/30; C07D 311/32
[52] U.S. Cl. ............ 514/457; 549/288; 549/289
[58] Field of Search ............ 514/457; 549/289, 549/288

[56] References Cited

U.S. PATENT DOCUMENTS 5,399,584  3/1995  Ares et al. .

OTHER PUBLICATIONS

Ares et al., J. Med. Chem., vol. 38, p. 4937–4943, 1995.

Gutierrez et al. Phytochemistry, vol. 39(4), p. 795–800, 1995.

*Primary Examiner*—Johann Richter
*Assistant Examiner*—Taofiq A. Solola
*Attorney, Agent, or Firm*—Bachman & LaPointe, P.C.

[57] ABSTRACT

The present invention relates to novel flavone/flavanone compounds or their pharmaceutically acceptable salts and process for preparation thereof for protecting gastrointestinal tracts against gastritis, ulcers and inflammatory bowel disease.

9 Claims, No Drawings

GASTROPROTECTIVE FLAVONE/ FLAVANONE COMPOUNDS WITH THERAPEUTIC EFFECT ON INFLAMMATORY BOWEL DISEASE

This application is a 371 of PCT/KR97/00144 filed Jul. 25, 1997.

FIELD OF THE INVENTION

The present invention relates to novel flavone/flavanone compounds or their pharmaceutically acceptable salts, and process for preparation thereof for protecting gastrointestinal tracts against gastritis, ulcers and inflammatory bowel disease.

BACKGROUND OF THE INVENTION

Although the incidence of gastric ulceration, duodenal ulceration or gastritis has been declining over the last decade, about 10% of the population will develop this condition at some time during their lives. The precise cause of these diseases remains uncertain despite of intensive clinical and laboratory research, but it is explained that they are induced from imbalance in equlibrium between potentially damaging factor present in the lumen of the stomach or duodenum and the process which enable these tissues to resist autodigestion.

The first line therapy for gastritis and gastric ulcer is to promote the effects of treatments by attenuating the attacking factors by administering antisecretory agents such as antacid, H2 antagonists and proton pump inhibitors. However, it has been reported that in the cases of omeprazole or long acting H2 antagonists, the duration of action was so long more than 24 hours that their long-term administration to rats caused dysplasia in epidermal cells of mucous membrane in gastrointestinal tracts (Ekman, L. et al., Scand. J. Gastroentrol.1985, 20 suppl.108: 53). And long-term administration of antisecretory agents is frequently associated with formation of gastric tumors in animals (Garner, A., Advances in Drug Therapy of Gastrointestinal Ulceration; Garner, A. and Whittle, B. J. R.(Eds.), Wiley & Sons, 1989, 275–88). Furthermore, a majority of patients with peptic ulcer disease have acid outputs within the normal range (Baron, J. H., Clinical Tests of Gastric Secretion. Macmillan, London, 1978, 86–119), so the treatments with antisecretory agents are not fundamental therapy and have a little effect on the prevention of recurrence, though they enhance acute healing of ulcer.

On the contrary cytoprotective agents such as sucralfate showed low frequency of recurrence (Marks, I. N., et al., Scand. J. Gastroentrol. 1983, 18 Suppl.83: 53. Shorrock, C. J., et al., Gut 1990, 31: 26), which implies that stimulating of mucosal defence is more desirable than attenuating the attacking factors for treatment of these diseases.

The anti-ulcer action without antisecretory activity is referred to as 'cytoprotection'. This cytoprotection is known to be due to the function of prostaglandins released from the gastric mucous membrane (Robert, A., 1981. Gastroenterology,16 Suppl.67: 223). Various kinds of prostaglandins such as $PEI_2$, $PGE_2$ are mainly generated in the gastric mucosa, and they effectively prevent the experimental ulceration induced by various kinds of ulcerogens (Robert. A., 1976. Advances in Prostaglandin and Thromboxane Research, Raven Press, New York, Vol 2, p.507). It was clinically proved that misoprostol, one of the prostaglandin compounds, prevented the gastric ulcer induced by NSAIDs (Graham, D. Y., et al., Lancet 1988, 2: 1277; Edelson, J. T., et al., JAMA 1990, 264: 41).

The cytoprotective mechanism of prostaglandins includes stimulating the blood flow of gastric mucosa (Guth, P. H., et al., Gastroenterology, 1984, 87: 1083), promoting mucus secretion (Allen, A., et al., Gut 1980, 21: 249; Rees, W. D. W., et al., Clin. Sci. 1982, 62: 343), promoting the gastric alkali secretion (Dayton, M. T., et al., Dig. Dis. Sci. 1983, 28; 449; Miller, T. A., et al., ibid 1983, 28; 641), preventing against the destruction of the gastric mucous defenses (Cheung, L. Y., Prostaglandins 1981, 21: 125), promoting the active transportation of sodium (Chaudhury, T. K., et al., Dig. Dis. Sci. 1980, 25: 830), stabilizing the lysozymes (Ferguson, W. W., et al., Am. Surg. 1973, 177: 648), and so on.

It has been also suggested that the tissue damages of many organs are induced by reactive oxygen species, such as lipid peroxides (Fridrich J., Science, 1978, 201: 875; Halliwell B, et al., Lancet 1984, 1: 1396; Freeman B A, et al., Lab Invest, 1982, 47: 412). And it was demonstrated that free radical scavengers have effects on protecting mucosa from damages induced by ischemic reperfusion (Peery, M. A., et al., Gastroentero logy, 1986, 90: 362), and then two enzymic antioxidants SOD and catalase could significantly reduce the extent of gastric mucosal damage induced by NSAIDs (Pihan, G., et al., Dig Dis Sci, 1987, 32:1395). It has been known that NSAIDs such as indomethacin induce adherence of leukocytes to the vascular endothelium and activation of neutrophils is accompanied by release of the active oxygens which can damage the gastrointestinal tracts (Klebanoff, S. J., Inflammation: Basic Principles and Clinical Correlates, New York: Raven, 1988, p.391–444; Vaananen P. M, et al., Am. J. Physiol., 1991, 256: G470–G475).

Particularly, it has been known that the active oxygens play an important role in the mucosal damage of inflammatory bowel disease (Simmonds N. J, et al., Gastroenterology, 1992, 103: 186), duodenal ulcer(Salim A. S, Dig. Dis. Sci., 1989, 35: 73), and *Helicobacter pylori*-induced gastric ulcer (Mooney C., et al., Gut, 1991, 32: 853).

Inflammatory bowel diseases, which are idiopathic chronic and refractory diseases having high relapsy, include ulcerative colitis and Crohn's disease. Though pathophysiology of the inflammatory bowel diseases remains unclear, inflammatory mediators such as leukotrienes is known to induce sustaining inflammation on the mucous membrane (Rachmilewitz, D., et al., Gastroenterology, 1989, 97: 326) as well as reactive oxygen species (Keshavarzian A., et al., Gastroenterology, 1992, 103: 177). Actually leukotriene inhibitors (Wallace J. L., et al., Gastroenterology, 1989, 96: 29; Zingarelli B, et al., Agents Actions 1993, 39: 150) reduced the damage of inflamed colon effectively.

On the other hand, flavonoid compounds which exist in nature show various effects, for example natural flavonoids such as hypolaetin-8-glucoside, apigenin-7,4'-dimethylether, kampferol, quercetin, naringenin, and hesperidine are known to have anti-ulcerative action (J.Pharm. Pharmacol.1984, 36: 820; Ind. J. Pharm. Sci. 1981, 43: 159; Ind. J. Exp. Biol. 1988, 26: 121; Phytotherapy Res.1992, 6: 168; ibid, 1988, 2: 137).

It has also been reported by Ares et al.(1995) that synthetic flavone derivatives such as 4'-fluoro-5-methoxy flavone, provide protective effect on the damage of gastric mucosa (U.S. Pat. No. 5,399,584).

We, the inventors of the present invention have synthesized many flavonoid compounds and screened, since small change of chemical structure of flavonoids can lead to different biological effects. And we have discovered that the appropriately substituted flavone/flavanone compounds in the formula(I) and their salts have better function of cytoprotection on gastrointestinal tracts including large intestine, than known compounds of flavone/flavanone.

SUMMARY OF THE INVENTION

The present invention is to provide flavone/flavanone compounds of the formula(I) and their pharmaceutically acceptable salts.

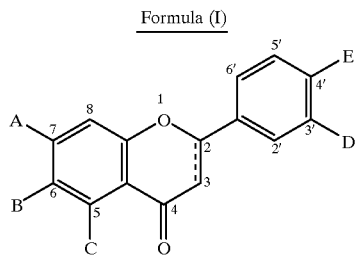

Formula (I)

In the structure of the formula(I), A, B and C, which are the same or different, are respectively selected from a group consisting of hydrogen, hydroxy, unsubstituted or monosubstituted alkyloxy or cycloalkyloxy group. The preferable substituents of alkyloxy groups contain hydroxy, carboxy, alkylester of carboxy, carboxamide, N-mono or dialkyl carboxamide, N-hydroxy carboxamide, N-hydroxy N-alkyl carboxamide, and substituted or unsubstituted benzene ring.

D and E, which are the same or different, are respectively selected from a group consisting of hydrogen, hydroxy, low alkyloxy having normal or branched chain with one to six carbon atoms.

And the bond between 2- and 3-position is single or double.

The present invention is also to provide process for preparing flavone/flavanone compounds and their pharmaceutically acceptable salts.

The present invention is also to provide uses of flavone/flavanone compounds having formula(I) or their pharmaceutically acceptable salts to treat gastrointestinal diseases such as gastritis and gastric ulcer, and inflammatory bowel diseases such as ulcerative colitis and Crohn's disease.

DETAILED DESCRIPTION OF THE INVENTION

Flavone/flavanone derivatives of the structures of the formula(I) of the present invention are prepared as following. The numbers for the position of substituents are shown in the formula(I).

Flavone/flavanone derivatives of the formula(I) are obtained by the process which comprises aldolcondensation of 2-hydroxyacetophenone having appropriately substituted group A, B and C with benzaldehyde having appropriately substituted group D and E into forming chalcone, and followed by cyclization of the chalcone to form the skeletal structure of formula(I), removal of the protecting group of corresponding substituent of flavone/flavanone compounds of the formula(I), and introduction of the intended substituents at the deprotected positions.

Flavone derivatives having double bond between 2-position and 3-position are prepared by stirring the chalcone having formula(IV) with selenium dioxide in the refluxing isoamylalcohol or dimethylsulfoxide as solvent. While flavanone derivatives having single bond between 2-position and 3-position can be obtained by treatment with sulfuric acid.

Preparation of the compounds can be classified as follows according to the substituents A, B, C, D and E. <1> In case that A and C are respectively hydroxy or substituted or unsubstituted alkyloxy groups, the compounds are prepared by the following scheme.

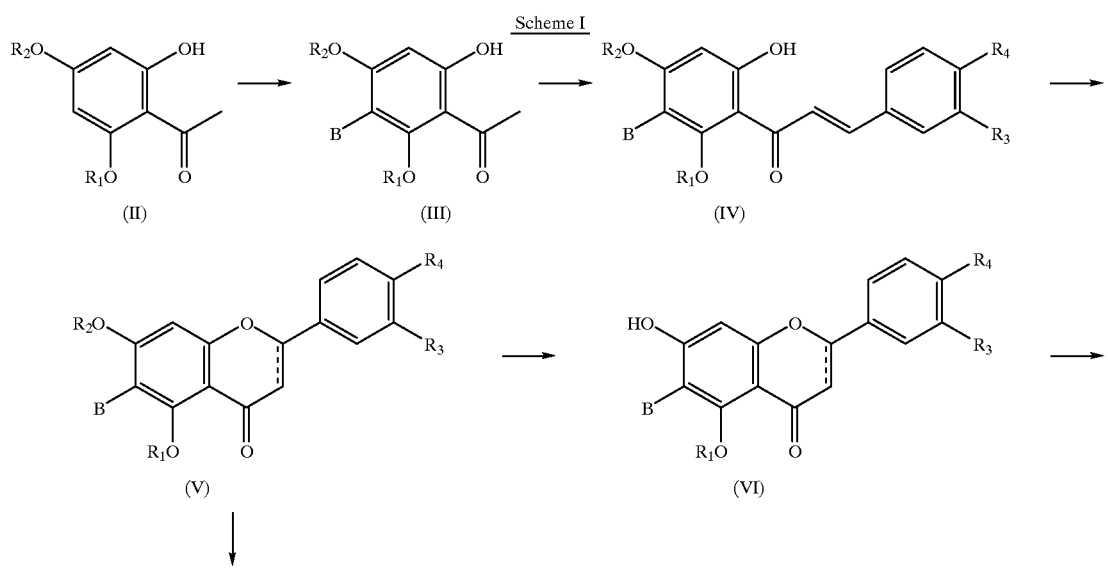

Scheme I

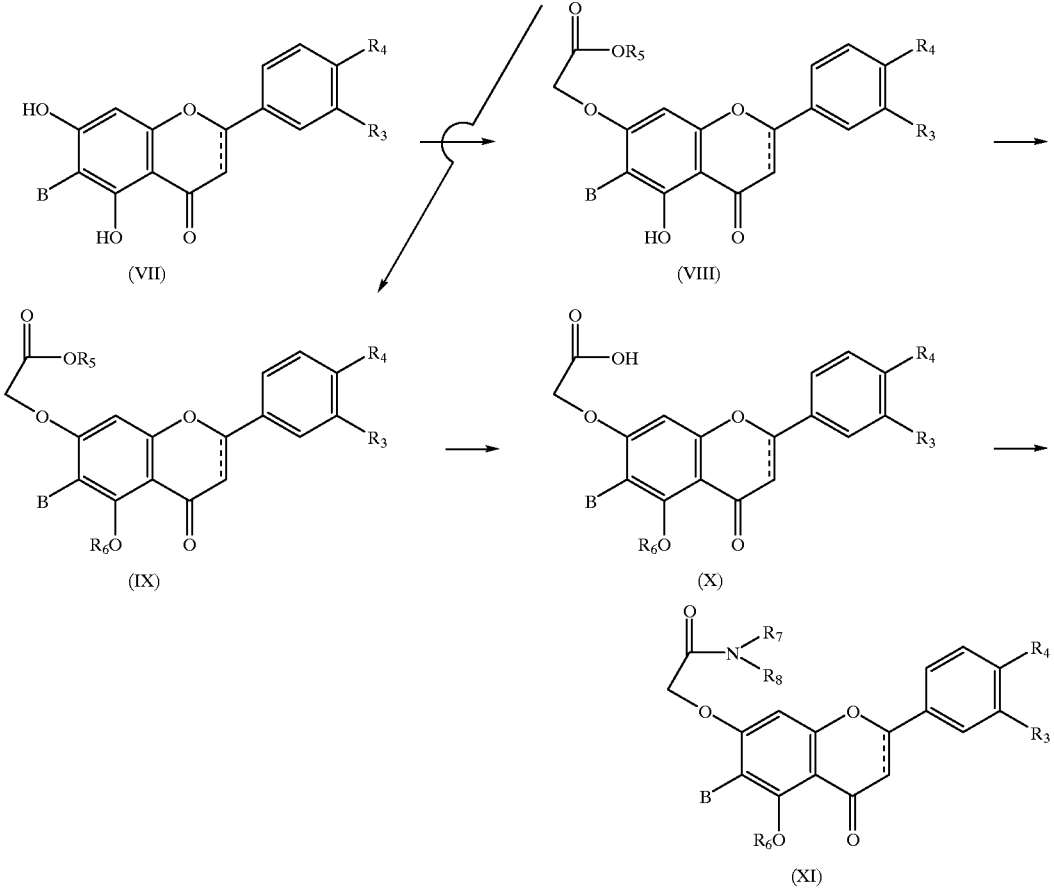

In case that B is not hydrogen but alkyloxy group, hydroxy group is introduced to the compound II as shown on the scheme 1 by Elbs persulfate oxidation(J. Org. Chem. 1984, 49: 645). Base which can be used in the above reaction is preferably selected from a group consisting of sodium hydroxide aqueous solution and tetraalkylammonium hydroxide aqueous solution. The appropriately substituted compound III is obtained by alkylating the introduced hydroxy group with appropriate alkylating agent, and the compound IV is obtained by aldol condensation of compound III with benzaldehyde which is appropriately substituted with $R_3$ and $R_4$. Solvents which can be used for aldol condensation are lower alcohol such as methanol and ethanol and the mixed solvent of the mentioned alcohol with water.

Compound V, flavone derivatives is obtained by heating the mixture of compound IV and selenium dioxide to reflux in the isoamylalcohol or dimethylsulfoxide as solvent. On the other hand, compound V which has single bond between 2- and 3-position, flavanone derivatives is obtained by reacting compound IV with sulfuric acid.

$R_1$ and $R_2$ which are either same or different, represent the appropriate protecting groups of phenoxy group such as methyl, benzyl, and benzoyl or appropriate alkyl or cycloalkyl groups. In case that $R_1$ and $R_2$ are respectively different protecting groups, they can be removed simultaneously (V→VI) or successively (V→VI→VII) by changing the reaction condition. For example, if $R_1$ is methyl group and $R_2$ is benzyl group, $R_1$ is successively removed by Lewis acid such as aluminum chloride after $R_2$ is selectively removed by reaction with hydrogen using metal catalyst, or $R_1$ and $R_2$ can be simultaneously removed using boron trichloride or hydrochloric acid with acetic acid.

The protecting group of phenoxy group can be simultaneously or successively removed by the mentioned process. Compound VIII selectively alkylated on the 7-position hydroxy group is obtained by reacting compound VI or VII with an equivalent of α-haloacetate in the presence of base in polar solvent.

Compound IX selectively alkylated on the 5-position hydroxy group is obtained by reacting compound VIII with alkylhalide $R_4X$ in the presence of base in polar solvent such as DMF.

Compound X can be prepared by removal of carboxyl protecting group and the compound XI is obtained by condensation the compound X with $R_7R_8NH$, wherein $R_7$ and $R_8$ which are respectively same or different, are selected from hydrogen, alkyl, hydroxy or alkoxy group. The condensation can be carried out by dehydration reaction using DCC (dicyclohexyl carbodiimide) or EDC (1-(3-dimethylaminopropyl)-3-ethyl-carbodiimide) or compound X can be converted to reactive carboxylic acid derivatives such as acid anhydride or acid chloride and then reacting it with $R_7R_8NH$ to give compound XI.

<2> In case that A, B and C are respectively hydrogen, the corresponding compounds are synthesized from appropriately substituted 2-hydroxyacetophenone through the similar process to scheme I.

The present invention is described in detail by the examples as following. Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

I. In case that A is hydroxy, B is alkoxy, and C, D and E are hydrogen, hydroxy, or alkoxy, respectively 1. Preparation of flavone derivatives

EXAMPLE 1

7-hydroxy-3',4',5,6-tetramethoxy flavone

1) Preparation of 4-benzyloxy-2,5-dihydroxy-6-methoxy acetophenone 4-benzyloxy-2-hydroxy-6-methoxy acetophenone (14.83 g, 54.5 mmol) was dissolved in the mixture of 35% tetraethylammonium hydroxide aqueous solution (291.7 mL, 13 equivalents) and pyridine (33.4 mL, 7.6 equivalents). To this mixture was slowly added the suspension of potassium persulfate (26 g, 1.7 equivalents) in 300 mL of water and reaction solution was stirred for 24 hours at room temperature. Then, concentrated hydrochloric acid was added to the reaction solution to adjust the pH of the solution into pH 1 to 2 at 0° C. and the solution was filtered under reduced pressure. After washing the resultant solution once with diethylether, hereto were added 5.8 g of sodium sulfite, 56.4 mL of concentrated hydrogen chloride and 113 mL of benzene and the mixture was refluxed for 30 minutes.

After cooling the solution to room temperature and extracting it with diethylether or ethyl acetate, the organic layer was dried over anhydrous magnesium sulfate, the solvent was removed by evaporation under reduced pressure to give the titled product (7 g, 45%).

NMR(CDCl$_3$): 13.11(s, 1H), 7.3(m, 5H), 6.32(s, 1H), 5.11(s, 2H), 4.64(brs, 1H), 3.95(s, 3H), 2.66(s, 3H).

2) Preparation of 4-benzyloxy-2-hydroxy-5,6-dimethoxy acetophenone 4-benzyloxy-2,5-dihydroxy-6-methoxyacetophenone (2.1 g, 7.3 mmol) was dissolved in 24 mL of acetone and hereto was added dimehtyl sulfate (0.68 mL, 0.9 equivalents). The solution was refluxed for 5 hours and cooled to room temperature. Acetone was removed by evaporation under reduced pressure, and then the residue was diluted with ethyl acetate and washed with water. The organic layer was dried over anhydrous magnesium sulfate, the solvent was removed by evaporation under reduced pressure to furnish the titled product (1.7 g, 77%).

NMR(CDCl$_3$): 13.36(s, 1H), 7.33(m, 5H), 6.27(s, 1H), 5.11(s, 2H), 3.99(s, 3H), 3.78 (s, 3H), 2.63(s, 3H).

3) Preparation of 4-benzyloxy-2-hydroxy-3',4',5,6-tetra methoxy chalcone

After 4-benzyloxy-2-hydroxy-5,6-dimethoxy acetophenone(1.6 g, 5.3 mmol) and 3,4-dimethoxybenzaldehyde (1 g, 1.2 equivalents) was suspended to 15 mL of ethanol, hereto was slowly added the solution of potassium hydroxide (3 g) in 15 mL of water. After the resultant solution was stirred at room temperature for 24 hours and concentrated, the residue was diluted with the solution of sodium bisulfate and washed with brine. After the organic layer was dried over anhydrous magnesium sulfate and the solvent was removed under reduced pressure, the residue was recrystallized in ethanol to afford 1.8 g of the titled product (75%).

NMR(CDCl$_3$): 13.66(s, 1 H), 7.80(s, 2H), 7.4(m, 5H), 7.19(m, 2H), 6.89(d, J=8.3 Hz, 1H), 6.34(s, 1H), 5.13(s, 2H), 3.92(s, 6H), 3.90(s, 3H), 3.84(s, 3H).

4) Preparation of 7-benzyloxy-3',4',5,6-tetramethoxy flavone

After 4-benzyloxy-2-hydroxy-3',4',5,6-tetramethoxy chalcone (1.6235 g, 3.6 mmol) was suspended to 52 mL of isoamylalcohol and selenium dioxide (4 g, 10 equivalents) was added at room temperature, and the mixture was refluxed for 7 hours. After the solution was cooled to room temperature and filtered through celite under reduced pressure,isoamylalcohol was removed by evaporation under reduced pressure and the residue was diluted with chloroform and washed sequentially with water, saturated sodium bicarbonate solution, and brine. Then, the resulting organic layer was dried and the solvent was removed. The residue was column-chromatographed to give 1.24 g of the titled product (77%).

NMR(CDCl$_3$): 7.33(m, 7H), 6.93(d, J=8.6 Hz, 1H), 6.83 (s,1H), 6.55(s, 1H), 5.20(5, 2H), 3.98(s, 3H), 3.94(s, 3H), 3.92(s, 3H) 3.90(s, 3H).

5) Preparation of 7-hydroxy-3',4',5,6-tetramethoxy flavone 7-benzyloxy-3',4',5,6-tetramethoxy flavone (5.62 g, 12.5 mmol) was dissolved in chloroform, hereto was added 10% Pd/C (1.06 g, 0.08 equivalents) and the mixture was stirred under hydrogen atmosphere at room temperature. After the reaction was completed, the reaction mixture was filtered through celite pad and the solvent was removed by evaporation to give 4.44 g of the titled product (98%).

NMR(CDCl$_3$): 7.35(dd, 1H), 7.29(d, J=2.0 Hz, 1H), 6.94 (d, J=8.5 Hz, 1H), 6.87(s, 1H) 6.56(s, 1H), 4.01(s, 3H), 3.96(s, 3H), 3.94(s, 3H), 3.92(s, 3H).

EXAMPLE 2

5,7-dihydroxy-3',4',6-trimethoxy flavone

After 7-hydroxy-3',4',5,6-tetramethoxy flavone (4.44 g, 12.4 mmol) was suspended in 88 mL of acetonitrile and aluminum trichloride (8.27 g, 5 equivalents) was added hereto at room temperature, the reaction mixture was refluxed for 1.5 hour and the solvent was removed by evaporation under reduced pressure. To the residue was added 10% aqueous solution of hydrochloric acid and chloroform, then the solution was refluxed until it became clear. After the solution was cooled to room temperature, the organic layer was washed with water and brine, then dried over anhydrous magnesium sulfate and the solvent of the organic layer was removed by reduced pressure. The residue was recrystallized in methanol to afford 3.18 g of the product (74%).

NMR(CDCl$_3$): 13.05(s,1H), 7.50(dd, J=8.6, 2.2 Hz, 1H), 7.31(d, J=2.1 Hz, 1H), 6.96(d, J=8.5 Hz, 1H), 6.59(s, 1H), 6.56(s, 1H), 6.48(br s, 1H), 4.03(s, 3H), 3.96(s, 3H), 3.95(s, 1H).

EXAMPLE 3

7-hydroxy-3',4',5-trimethoxy-6-n-propyloxy flavone

The titled product was synthesized from 4-benzyl oxy-2,5-dihydroxy-6-methoxy acetophenone as a starting material by the same process of the steps 2), 3), 4), and 5) of the Example 1.

1) Preparation of 4-benzyloxy-2-hydroxy-6-methoxy-5-n-propyloxy acetophenone

NMR(CDCl$_3$): 13.34(s, 1H), 7.37(m, 5H), 6.28(s, 1H), 5.09(s, 2H), 3.98(s, 3H), 3.85(t,J=6.6 Hz, 1H), 2.63(s, 3H), 1.74(m, 2H), 0.98(t, J=7.5 Hz, 1H).

2) Preparation of 4-benzyloxy-2-hydroxy-3',4',6-trimethoxy-5-n-propyloxy chalcone NMR(CDCl$_3$): 13.70(s, 1H), 7.80(q, 2H), 7.39(m, 5H), 7.23(dd, 1H), 7.14 (d, J=1.8 Hz, 1H), 6.89(d, J=8.3 Hz, 1H), 6.34(s, 1H), 5.12(s, 1H), 3.9(m, 11H), 1.77(m, 2H) 1.00(t, J=7.4 Hz, 3H).

3) Preparation of 7-benzyloxy-3',4',5-trimethoxy-6-n-propyloxy flavone

NMR(CDCl$_3$): 7.42(m, 7H), 6.95(d, J=8.4 Hz, 1H), 6.84 (s, 1H), 6.56(s, 1H), 5.20(s, 2H), 3.99(t, 2H), 3.98(s, 3H), 3.95(s,3H), 3.94(s, 3H), 1.77(m, 2H), 1.01(t, J=7.3 Hz, 3H).

4) Preparation of 7-hydroxy-3',4',5-trimethoxy-6-n-propyloxy flavone

NMR(CDCl$_3$): 7.48(dd, 1H), 7.30(d, J=2.2 Hz, 1H), 6.95 (d, J=8.5 Hz, 1H), 6.56(s, 1H), 6.38(s, 1H), 4.17(t, J=6.6 Hz, 1H), 3.95(s, 6H), 3.94(s, 3H), 1.80(m, 2H), 1.03(t, J=7.3 Hz, 3H).

EXAMPLE 4

5,7-dihydroxy-3',4'-dimethoxy-6-n-propyloxy flavone

The titled product was synthesized from 7-hydroxy-3',4',5-trimethoxy-6-n-propylflavone as a starting material by the same process of the Example 2.

NMR(CDCl$_3$): 13.04(s,1H) 7.48(dd,1H), 7.32(d, J=2.1 Hz, 1H), 6.96(d, J=8.5 Hz, 1H), 6.59(s, 1H), 6.55(s, 1H), 6.49 (s, 1H), 4.21(t, J=6.8 Hz, 2H), 3.96(s,3H), 3.95(s, 3H), 1.80(m, 2H), 1.03(t, J=7.4 Hz, 3H).

EXAMPLE 5

7-hydroxy-3',4',5-trimethoxy-6-n-pentyloxy flavone

The titled product was synthesized from 4-benzyloxy-2,5-dihydroxy-6-methoxy acetophenone as a starting material by the same process of the Example 3.

1) Preparation of 4-benzyloxy-2-hydroxy-6-methoxy-5-n-pentyloxy acetophenone

NMR(CDCl$_3$): 13.36 (s, 1H), 7.37(m, 5H), 6.28(s, 1H), 5.08(s, 2H), 3.97(s, 3H), 3.88(t,J=6.6 Hz, 2H), 2.63(s, 3H), 1.71(m, 2H), 1.36(m, 4H), 0.86(t, J=6.8 Hz, 3H).

2) Preparation of 4-benzyloxy-2-hydroxy-3',4',6-trimethoxy-5-n-pentyloxy chalcone NMR(CDCl$_3$): 13.69 (s, 1H), 7.80(q, 2H), 7.40(m, 5H), 7.22 (dd, 1H), 7.14(d, J=1.8 Hz, 1H), 6.34(s, 1H), 5.11(s, 2H), 3.94(t, 2H), 3,93(s, 3H), 3.92(s, 6H), 1.74(m, 2H), 1.31(m, 4H), 0.87(t, J=6.9 Hz, 3H).

3) Preparation of 7-benzyloxy-3',4',5-trimethoxy-6-n-pentyloxy flavone

NMR(CDCl$_3$): 7.39(m, 7H), 6.95(d, J=8.4 Hz, 1H), 6.84 (s, 1H), 6.56(s, 1H), 5.19(s, 2H), 4.03(t, J=6.5 Hz, 2H), 3.97(s, 3H), 3.95(s, 3H), 3.94(s, 3H), 1.77(m, 2H), 1.39(m, 4H), 0.86(t, J=6.9 Hz, 3H).

4) Preparation of 7-hydroxy-3',4',5-trimethoxy- 6-n-pentyloxy flavone

NMR(CDCl$_3$): 7.48(dd, 1H), 7.30(d, J=2.1 Hz, 1H), 6.95 (d, J=8.6 Hz, 1H), 6.87(s, 1H), 6.56(s, 1H), 6.40 (s,1H), 4.20(t, J=6.8 Hz, 2H), 3.95(s, 6H), 3.94(s, 3H), 1.77(m, 2H), 1.42(m, 4H), 0.91(t, 3H).

EXAMPLE 6

5,7-dihydroxy-3',4'-dimethoxy-6-n-pentyloxy flavone

The titled product was synthesized from 7-hydroxy-3',4',5-trimethoxy-6-n-pentyloxy flavone as a starting material by the same process of the Example 2.

NMR(CDCl$_3$): 13.01(s, 1H), 7.47(dd, J=8.4, 2.1 Hz, 1H), 7.29(d, J=2.0 Hz, 1H), 6.94(d, J=8.5 Hz, 1H), 6.58(s, 1H), 6.57(s, 1H), 6.53(s, 1H), 4.22(t, J=6.7 Hz, 2H), 3.94(s, 3H), 3.93(s,3H), 1.77(m, 2H) 1.39(m, 4H), 0.91(t, J=6.9 Hz, 3H).

EXAMPLE 7

6-ethoxy-7-hydroxy-3',4',5-trimethoxy flavone

The titled product was synthesized from 4-benzyloxy-2,5-dihydroxy-6-methoxy acetophenone as a starting material by the same process of the Example 3.

1) Preparation of 4-benzyloxy-5-ethoxy-2-hydroxy-6-methoxy acetophenone

NMR(CDCl$_3$): 13.35(s, 1H), 7.35(m, 5H), 6.27(s, 1H), 5.10(s, 2H), 3.99(s, 3H), 3.97(q, 2H), 2.63(s, 3H), 1.34(t, J=6.9 Hz, 1H).

2) Preparation of 4-benzyloxy-5-ethoxy-2-hydroxy-3',4',6-trimethoxy chalcone

NMR(CDCl$_3$): 13.64(s, 1H), 7.80(s, 2H), 7.36(m, 5H), 7.23(dd, 1H), 7.14 (d, J=2.0 Hz, 1H), 6.89(d, J=8.3 Hz, 1H), 6.34(s, 1H), 5.12(s, 2H), 4.03(q, J=7.1 Hz, 2H), 3.94(s, 3H), 3.93(s, 3H), 3.92(s, 3H), 1.37(t, J=6.5 Hz, 3H).

3) Preparation of 7-benzyloxy-6-ethoxy-3',4',5-trimethoxy flavone

NMR(CDCl$_3$): 7.37(m, 7H), 6.95(d, J=8.5 Hz, 1H), 6.84 (s, 1H), 6.56(s, 1H), 5.20(s, 2H), 4.13(q, J=7.1 Hz, 2H), 3.99(s, 3H), 3.96(s, 3H), 3.94(s, 3H), 1.37(t, J=6.9 Hz, 3H).

4) Preparation of 6-ethoxy-7-hydroxy-3',4',5-trimethoxy flavone

NMR(CDCl$_3$): 7.48(dd, 1H), 7.30(d, J=2.1 Hz, 1H), 6.95 (d, J=8.5 Hz, 1H), 6.87(s, 1H), 6.55(s, 1H), 6.38(s, 1H), 4.30(q, J=7.0 Hz, 1H), 3.96(s, 3H), 3.95(s, 3H), 3.94(s, 3H), 1.39(t, J=7.0 Hz, 3H).

EXAMPLE 8

6-ethoxy-5,7-dihydroxy-3',4'-dimethoxy flavone

The titled product was synthesized from 6-ethoxy-7-hydroxy-3',4',5-trimethoxy flavone as a starting material by the same process of the Example 2.

NMR(CDCl$_3$): 13.03(s, 1H), 7.48(dd, J=8.5, 2.0 Hz, 1H), 7.30(d, J=2.0 Hz, 1H), 6.95(d, J=8.5 Hz, 1H), 6.58(s, 1H), 6.56(s, 1H), 6.54(s, 1H), 4.31(q, J=7.0 Hz, 2H), 3.95(s, 3H), 3.94(s, 3H), 1.38(t, J=6.9 Hz, 3H).

EXAMPLE 9

6-n-butyloxy-7-hydroxy-3',4',5-trimethoxy flavone

The titled product was synthesized from 4-benzyloxy-2,5-dihydroxy-6-methoxy acetophenone as a starting material by the same process of the Example 3.

1) Preparation of 4-benzyloxy-5-n-butyloxy-2-hydroxy-6-methoxy acetophenone

NMR(CDCl$_3$): 13.33 (s, 1H), 7.35(m, 5H), 6.28(s, 1H), 5.09(s, 2H), 3.97(s, 3H), 3.87(t, 2H), 2.63(s, 3H), 1.69(m, 2H), 1.45(m, 2H), 0.90(t, 3H).

2) Preparation of 4-benzyloxy-5-n-butyloxy-2-hydroxy-3',4',6-trimethoxy chalcone NMR(CDCl$_3$): 13.69(s, 1H), 7.80(d, 2H), 7.37(m, 5H), 7.23(dd, 1H), 7.14(d, J=1.9 Hz, 1H), 6.89(d, J=8.3 Hz, 1H), 6.34(s, 1H), 5.11(s, 2H), 3.94(t, 2H), 3.93(s, 3H), 3.92(s, 6H), 1.71(m, 2H), 1.42(m, 2H), 0.91(t, J=7.3 Hz, 3H).

3) Preparation of 7-benzyloxy-6-n-butyloxy-3',4',5-trimethoxy flavone

NMR(CDCl$_3$): 7.38(m, 7H), 6.95(d, J=8.5 Hz, 1H), 6.84 (s, 1H), 6.57(s, 1H), 5.19(s, 2H), 4.04(t, J=6.4 Hz, 2H), 3.97(s, 3H), 3.96(s, 3H), 3.94(s, 3H), 1.75(m, 2H), 1.52(m, 2H), 0.90(t, J=7.3 Hz, 3H).

4) Preparation of 6-n-butyloxy-7-hydroxy-3',4',5-trimethoxy flavone

NMR(CDCl$_3$): 7.50(dd, 1H), 7.32(d, 1H), 6.95(d, 1H), 6.87(s, 1H), 6.56(s, 1H), 6.37(s, 1H), 4.21(t, 2H), 3.95(s, 6H), 3.94(s, 3H), 1.76(m, 2H), 1.51(m, 2H), 0.97(t, J=7.3 Hz, 3H).

EXAMPLE 10

6-n-butyloxy-5,7-dihydroxy-3',4'-dimethoxy flavone

The titled product was synthesized from 6-n-butyloxy-7-hydroxy-3',4',5-trimethoxy flavone as a starting material by the same process of the Example 2.

NMR(CDCl$_3$): 13.00(s, 1H), 7.47(dd, 1H), 7.29(d, 1H), 6.93(d, J=8.5 Hz, 1H), 6.57(br s, 1H), 6.56(s, 1H), 6.53(s,

1H), 4.22(t, J=6.66 Hz, 2H), 3.94(s, 3H), 3.92(s, 3H), 1.73(m, 2H), 1.45(m, 2H), 0.95(t, J=7.3 Hz, 3H).

EXAMPLE 11
7-hydroxy-4',5,6-trimethoxy flavone

The titled product was synthesized from 4-benzyloxy-2-hydroxy-5,6-dimethoxy acetophenone as a starting material by the same process of the Example 3.

1) Preparation of 4-benzyloxy-2-hydroxy-4',5,6-trimethoxy chalcone

NMR(CDCl$_3$): 13.66(s, 1H), 7.82(s, 2H), 7.58(d, J=8.7 Hz, 2H), 7.38(m,5H) 6.92(d, J=8.7 Hz, 2H), 6.33(s, 1H), 5.13(s, 2H), 3.92(s, 3H), 3.84(s, 6H).

2) Preparation of 7-benzyloxy-4',5,6-trimethoxy flavone

NMR (CDCl$_3$): 7.78(d, 2H), 7.38(m, 5H), 6.97(d, 2H), 6.82(s, 1H), 6.54(s, 1H), 6.21(s, 2H), 3.98(s, 3H), 3.91(s, 3H), 3.86 (s, 3H).

3) Preparation of 7-hydroxy-4',5,6-trimethoxy flavone

NMR(CDCl$_3$): 7.79(d, J=9.1 Hz, 2H), 6.98(d, J=8.9 Hz, 2H), 6.85(s, 1H), 6.55(s, 1H), 6.46(s, 1H), 4.02(s, 3H), 3.96(s, 3H), 3.86(s, 3H).

EXAMPLE 12
5,7-dihydroxy-4',6-dimethoxy flavone

The titled product was synthesized from 7-hydroxy-4',5,6-trimethoxy flavone as a starting material by the same process of the Example 2.

NMR(CDCl$_3$): 13.08(s, 1H), 7.82(d, J=9.0 Hz, 2H), 7.00 (d, J=8.9 Hz, 2H), 6.57(s, 1H), 6.55(s, 1H), 6.49(s, 1H), 4.03(s, 3H), 3.87(s, 3H).

EXAMPLE 13
7-hydroxy-5,6-dimethoxy flavone

The titled product was synthesized from 4-benzyloxy-2-hydroxy-5,6-dimethoxy acetophenone as a starting material by the same process of the steps 3), 4) and 5) of the Example 1.

1) Preparation of 4-benzyloxy-2-hydroxy-5,6-dimethoxy chalcone

NMR(CDCl$_3$): 13.55(s, 1H), 7.95(d, 1H), 7.80(d, 1H), 7.45(m,10H), 6.34(s, 1H), 5.14(s, 2H), 3.94(s, 3H), 3.84(s, 3H).

2) Preparation of 7-benzyloxy-5,6-dimethoxy flavone

NMR(CDCl$_3$): 7.86(m, 2H), 7.45(m, 8H), 6.85(s, 1H), 6.64(s, 1H), 5.22(s, 2H), 3.99(s, 3H), 3.92(s, 3H).

3) Preparation of 7-hydroxy-5,6-dimethoxy flavone

NMR(CDCl$_3$): 7.84(m, 2H), 7.49(m, 3H), 6.88(s, 1H), 6.64(s, 1H), 6.42(s, 1H), 4.03(s, 3H), 3.97(s, 3H).

EXAMPLE 14
5,7-dihydroxy-6-methoxy flavone

The titled product was synthesized from 7-hydroxy-5,6-dimethoxy flavone as a starting material by the same process of the Example 2.

NMR(CDCl$_3$): 12.99(s, 1H), 7.87(m, 2H), 7.52(m, 3H), 6.64(s, 1H), 6.60(s, 1H), 6.50(s, 1H), 4.03(s, 3H).

EXAMPLE 15
3',7-dihydroxy-4',5,6-trimethoxy flavone

The titled product was synthesized from 4-benzyloxy-2-hydroxy-5,6-dimethoxy acetophenone as a starting material by the same process of the steps 3), 4) and 5) of the Example 1.

1) Preparation of 3',4-dibenzyloxy-2-hydroxy-4',5,6-trimethoxychalcone

NMR(CDCl$_3$): 13.61(s, 1H), 7.72(s, 2H), 7.33(m, 12H), 6.90(d, J=8.3 Hz, 1H) 6.33(s, 1H), 5.20(s, 2H), 5.13(s, 2H), 3.92(s, 3H), 3.85(s, 3H), 3.84(s, 3H).

2) Preparation of 3',7-dibenzyloxy-4',5,6-trimethoxy flavone

NMR(CDCl$_3$): 7.41(m, 12H), 6.96(d, J=8.6 Hz, 1H), 6.78(s, 1H), 6.49(s, 1H), 5.21(s, 2H), 5.20(s, 2H), 3.98(s, 3H), 3.94(s, 3H), 3.91(s, 3H).

3) Preparation of 3',7-dihydroxy-4',5,6-trimethoxy flavone

NMR(CDCl$_3$+DMSO-d$_6$+D$_2$O)): 7.27(m, 2H), 6.82(d, J=8.3 Hz, 1H), 6.72(s, 1H), 6.40(s, 1H), 3.84(s, 6H).

EXAMPLE 16
3',5,7-trihydroxy-4',6-dimethoxy flavone

The titled product was synthesized from 3',7-dihydroxy-4',5,6-trimethoxy flavone as a starting material by the same process of the Example 2.

NMR(CDCl$_3$): 12.96(br s, 1H), 10.45(br s, 1H), 9.31(br s, 1H), 7.45(dd J=8.9, 2.3 Hz, 1H), 7.37(d, J=2.3 Hz, 1H), 7.00(d, J=8.5 Hz, 1H), 6.60(s, 1H), 6.51(s, 1H), 3.86(s, 3H), 3.76(s, 3H).

EXAMPLE 17
7-hydroxy-3'4',6-trimethoxy flavone

The titled product was synthesized from 2-hydroxy-4-benzyloxy acetophenone as a starting material by the same process of the Example 1.

1) Preparation of 4-benzyloxy-2,5-dihydroxy acetophenone

NMR(CDCl$_3$): 12.41 (s, 1H), 7.35(m, 5H), 7.21(s, 1H), 6.51(s, 1H), 5.27(br s, 1H), 5.12(s, 2H), 2.51(s, 3H).

2) Preparation of 4-benzyloxy-2-hydroxy-5-methoxy acetophenone

NMR(CDCl$_3$): 12.54(s, 1H), 7.35(m, 5H), 7.09(s, 1H), 6.47(s, 1H), 5.16(s, 2H), 3.85(s, 3H), 2.53(s, 3H).

3) Preparation of 4-benzyloxy-2-hydroxy-3',4',5-trimethoxy chalcone

NMR(CDCl$_3$): 13.32(s, 1H), 7.49(m, 10H), 6.90(d, 1H), 6.54(s, 1H), 5.18(s, 2H), 3.94 (s, 3H), 3.92(s, 3H), 3.89(s, 3H).

4) Preparation of 7-benzyloxy-3',4',6-trimethoxy flavone

NMR(CDCl$_3$): 7.43(m, 8H), 7.00(s, 1H), 6.95(s, 1H), 6.69(s, 1H), 5.26(s, 2H), 3.97(s, 3H).

5) Preparation of 7-hydroxy-3',4',6-trimethoxy flavone

NMR(DMSO-d$_6$): 7.63(dd, 1H), 7.53(d, 1H), 7.35(s, 1H), 7.11(s, 1H), 7.05(d, 1H), 6.88(s, 1H), 3.87(s, 6H), 3.83(s, 3H).

EXAMPLE 18
3',4',7-trihydroxy-5,6-dimethoxy flavone

The titled product was synthesized from 4-benzyloxy-2-hydroxy-5,6-dimethoxy acetophenone as a starting material by the same process of the steps 3),4) and 5) of the Example 1.

1) Preparation of 3',4',4-tribenzyloxy-2-hydroxy-5,6-dimethoxy chalcone

NMR(CDCl$_3$): 13.63(s, 1H), 7.72(s, 2H), 7.33(m, 17H), 6.93(d, J=8.1 Hz, 1H), 6.33(s, 1H), 5.21(s, 4H), 5.13(s, 2H), 3.84(s, 6H).

2) Preparation of 3',4',7-tribenzyloxy-5,6-dimethoxy flavone

NMR(CDCl$_3$): 7.39(m, 17H), 6.92(d, J=8.2 Hz, 1H), 6.77(s,1H), 6.49(s, 1H), 5.21(s, 6H), 3.92(s, 3H), 3.91(s, 3H).

3) Preparation of 3',4',7-trihydroxy-5,6-dimethoxy flavone

NMR(DMSO-d$_6$): 10.67(bs, 1H), 7.33(s, 1H), 7.31(d, 1H), 6.86(d, 1H), 6.84(s, 1H), 6.42(s, 1H), 3.78(s, 3H), 3.76(s, 3H).

EXAMPLE 19
3',4',5,7-tetrahydroxy-6-methoxy flavone

The titled product was synthesized from 3',4',7-trihydroxy-5,6-dimethoxy flavone as a starting material by the same process of the Example 2.

NMR(DMSO-$d_6$): 13.07(br s, 1H), 10.68(br s, 1H), 9.89 (br s, 1H), 9.37(br s, 1H), 7.39(d, 1H), 7.38(s, 1H), 6.87(d, J=8.3 Hz, 1H), 6.65(s, 1H), 6.54(s, 1H), 3.74(s, 3H).

EXAMPLE 20
5-hydroxy-3',4',6,7-tetramethoxy flavone

The titled product was synthesized from 3',4',5,6,7-pentamethoxy flavone as a starting material by the same process of the Example 2.

NMR(CDCl$_3$): 12.73(s, 1H), 7.50(dd, J=8.5, 2.1 Hz, 1H), 7.32(d, J=2.1 Hz, 1H), 6.96(d, J=8.6 Hz, 1H), 6.58(s, 1H), 6.53(s, 1H), 3.97(s, 3H), 3.96(s, 3H), 3.94(s, 3H), 3.91(s, 3H).

EXAMPLE 21
7-hydroxy-6-n-pentyloxy flavone

The titled product was synthesized from 4-benzyloxy-2-hydroxy acetophenone as a starting material by the same process of the Example 1.

1) Preparation of 4-benzyloxy-2-hydroxy-5-n-pentyloxy chalcone

NMR(CDCl$_3$): 13.29(s, 1H), 7.58(m,13H), 6.53(s, 1H), 5.14(t, 2H), 4.01(t, J=6.5 Hz, 2H), 1.80(m, 2H), 1.40(m, 4H), 0.92(t, J=6.6 Hz, 3H).

2) Preparation of 7-benzyloxy-6-n-pentyloxy flavone

NMR(CDCl$_3$): 7.60(m, 11H), 7.01(s, 1H), 6.75(s, 1H), 5.25 (s, 2H), 4.12(t, J=6.6 Hz, 2H), 1.87(m, 2H), 1.40(m, 4H), 0.92(t, J=6.9 Hz, 3H).

3) Preparation of 7-hydroxy-6-n-pentyloxy flavone

NMR(CDCl$_3$): 7.90(m, 2H), 7.56(s, 1H), 7.50(m, 3H), 7.07(s, 1H), 6.76(s, 1H), 6.35(br s, 1H), 4.17(t, J=6.6 Hz, 2H), 1.83(m, 2H), 1.40(m,4H), 0.94(t, J=6.9 Hz, 3H).

EXAMPLE 22
7-hydroxy-3',4'-dimethoxy-6-n-pentyloxy flavone

The titled product was synthesized from 4-benzyloxy-2-hydroxy acetophenone as a starting material by the same process of the Example 1.

1) Preparation of 4-benzyloxy-2-hydroxy-3',4'-dimethoxy-5-n-pentyloxy chalcone

NMR(CDCl$_3$): 13.34(s, 1H), 7.36(m, 1H), 6.53(s, 1H), 5.15(s, 2H), 4.00(t, 2H), 3.95(s, 3H), 3.92(s, 3H), 1.75(m, 2H), 1.43(m, 4H), 0.92(t, 3H).

2) Preparation of 7-benzyloxy-3',4'-dimethoxy-6-n-pentyloxy flavone

NMR(CDCl$_3$): 7.21(m, 10H), 6.69(s, 1H), 5.25(s, 3H), 4.11(t, 2H), 3.96(s, 3H), 3.94(s, 3H), 1.87(m, 2H), 1.43(m, 4H), 0.91(t, 3H).

3) Preparationof 7-hydroxy-3',4'-dimethoxy-6-n-pentyloxy flavone

NMR(CDCl$_3$): 7.54(s, 1H), 7.51(dd, J=8.4, 2.1 Hz, 1H), 7.33(d, J=2.1 Hz, 1H), 7.06(s, 1H), 6.95(d, J=8.6 Hz, 1H), 6.68(s, 1H), 6.95(d, J=8.6 Hz, 1H), 6.68(s, 1H), 6.42(br s, 1H), 4.15(t, J=6.6 Hz, 2H), 3.95(s, 3H), 3.94(s, 3H), 1.85(m, 2H), 1.42(m, 4H), 0.92(t, J=6.9 Hz, 3H).

EXAMPLE 23
5,7-dihydroxy-6-methoxy-4'-thiomethoxy flavone

1) Preparation of 4-benzyloxy-2-hydroxy-5,6-dimethoxy-4'-thiomethoxy chalcone

The titled product was synthesized from 4-benzyloxy-2-hydroxy-5,6-dimethoxy acetophenone as a starting material by the same process of the step 3) of the Example 1.

NMR(CDCl$_3$): 13.61(s, 1H), 7.92(d, 1H), 7.77(d, 1H), 7.4(m, 9H), 6.33(s, 1H), 5.13(s, 2H), 3.92(s, 3H), 3.83(s, 3H), 2.59(s, 3H).

2) Preparation of 7-benzyloxy-5,6-dimethoxy-4'-thiomethoxy flavone

The titled product was synthesized from 4-benzyloxy-2-hydroxy-5,6-dimethoxy-4'-thiomethoxy chalcone as a starting material by the same process of the step 4) of the Example 1.

NMR(CDCl$_3$): 7.56(m, 9H), 6.83(s, 1H), 6.60(s, 1H), 5.21(s, 2H), 3.98(s, 3H), 3.91(s, 3H), 2.52(s, 3H).

3) The 5,7-dihydroxy-6-methoxy-4'-thiomethoxy flavone

The titled product was synthesized from 7-benzyloxy-5,6-dimethoxy-4'-thiomethoxy flavone as a starting material by the same process of the Example 2.

NMR(CDCl$_3$): 13.00(s, 1H), 7.76(d, 2H), 7.31(d, 2H), 6.59(s, 1H), 6.58(s, 1H), 4.02(s, 3H), 2.52(s, 3H).

2. Preparation of flavanone derivatives

EXAMPLE 24
5,7-dihydroxy-3',4',6-trimethoxy flavanone

1) Preparation of 7-benzyloxy-3',4',5,6-tetramethoxy flavanone 4-benzyloxy-2-hydroxy-3',4',5,6-tetramethoxy chalcone (2.5 g, 5.55 mmol) was suspended in 4% of sulfuric acid/methanol (150 mL) and chloroform was added hereto until the solution became clear. After the reaction solution was refluxed for 6 hours and the reaction solvent was removed under reduced pressure, the residue was diluted with chloroform and then washed with water. The organic layer was dried over anhydrous magnesium sulfate and the solvent was removed under reduced pressure. The residue was column-chromatographed to furnish 1.56 g of the titled product (62%).

NMR(CDCl$_3$): 7.39(m, 5H), 6.93(m, 3H), 6.38(s, 1H), 5.30(dd, 1H), 5.11(s, 2H), 3.93(s, 3H), 3.89(s, 3H), 3.88(s, 3H), 3.83(s, 3H), 3.03(dd, 1H), 2.75(dd, 1H).

2) Preparation of 5,7-dihydroxy-3',4',6-trimethoxy flavanone

The titled product was synthesized from 7-benzyloxy-3',4',5,6-tetramethoxy flavanone as a starting material by the same process of the Example 2.

NMR(CDCl$_3$): 12.17 (s, 1H), 6.90(m, 3H), 6.49(br s, 1H), 6.11(s, 1H), 5.32(dd, J=12.8, 3.1 Hz, 1H), 3.92(s, 3H), 3.90(s, 3H), 3.88(s, 3H), 3.10(dd, J=12.8 Hz, 1H), 2.79(dd, J=3.2 Hz, 1H).

EXAMPLE 25
7-hydroxy-6-n-pentyloxy flavanone

1) Preparation of 7-benzyloxy-6-n-pentyloxy flavanone

The titled product was synthesized from 4-benzyloxy-5-n-pentyloxy 2-hydroxy chalcone as a starting material by the same process of the step 1) of the Example 24.

NMR(CDCl$_3$): 7.35(m,1H), 6.53(s,1H), 5.40(dd, J=13.2, 3.2 Hz, 1H), 5.14(s,2H), 4.01(t,J=6.6 Hz, 2H), 3.00(dd,1H), 2.75(dd,1H), 1.82(m,2H), 1.41(m,4H), 0.91(t, J=6.8 Hz, 3H).

2) Preparation of 7-hydroxy-6-n-pentyloxy flavanone

The titled product was synthesized from 7-benzyloxy-5-n-pentyloxy flavanone as a starting material by the same process of the step 5) of the Example 1.

NMR(CDCl$_3$): 7.35(m, 6H), 6.57(s, 1H), 6.25(s, 1H), 5.42(dd, J=12.8, 3.4 Hz, 1H), 4.05(t, J=6.6 Hz, 2H), 3.01(dd, 1H), 2.80(dd, 1H), 1.81(m, 2H), 1.38(m, 4H), 0.92(t, 3H).

II. In case that A is hydroxy, B is hydrogen, C, D and E are hydrogen, hydroxy or alkyloxy, respectively 1. Preparation of flavone derivatives

EXAMPLE 26
7-hydroxy-3',4',5-trimethoxy flavone

The titled product was synthesized from 4-benzyloxy-2-hydroxy-6-methoxy acetophenone as a starting material by the same process of the steps 3), 4) and 5) of the Example 1.

1) Preparation of 4-benzyloxy-2-hydroxy-3',4',6-trimethoxy chalcone

NMR(CDCl$_3$): 14.32(s, 1H), 7.76(s, 2H), 7.37(m, 5H), 7.13(dd, J=8.4, 2.0 Hz, 1H), 7.11(d, J=1.8 Hz, 1H), 6.88(d, J=8.3 Hz, 1H), 6.18(d, J=2.3 Hz, 1H), 6.03(d, J=8.3 Hz, 1H), 5.07(s, 2H), 3.92(s, 3H), 3.91(s, 3H), 3.89(s, 3H).

2) Preparation of 7-benzyloxy-3',4',5-trimethoxy flavone

NMR(CDCl$_3$): 7.38(m, 7H), 6.94(d, J=8.6 Hz, 1H), 6.63 (d, J=2.2 Hz, 1H), 6.59(s, 1H), 6.44(d, J=2.3 Hz, 1H), 5.14(s, 2H), 3.95(s, 3H), 3.93(s, 6H).

3) Preparation of 7-hydroxy-3',4',5-trimethoxy flavone

NMR(+DMSO-d$_6$): 7.24(dd, 1H), 7.06(d, J=2.1 Hz, 1H), 6.71(d, J=8.5 Hz, 1H), 6.41(br s, 1H), 6.31(d, J=2.2 Hz, 1H), 6.13(d, J=2.0 Hz, 1H), 3.67(s, 3H), 3.66(s, 3H), 3.64(s, 3H).

EXAMPLE 27
5,7-dihydroxy-3',4'-dimethoxy flavone 7-benzyloxy-3',4',5-trimethoxy flavone (565 mg, 1.35 mmol) was dissolved in 17 mL of methylenechloride, and then 1M of boron trichloride (3.79 mL, 3 equivalents) was added at temperature of 0° C. Then the reaction mixture was stirred for 30 minutes. When aqueous sodium acetate solution (5 mL) was added to the resultant reaction mixture, the product was obtained as a yellow crystal. The product was triturated with hexane and filtered to give the titled product (271 mg, 64%).

NMR(DMSO-d$_6$): 12.90(s, 1H), 10.78(s, 1H), 7.67(dd, J=8.5, 2.0 Hz, 1H), 7.55(d, J=2.0 Hz, 1H), 7.12(d, J=8.6 Hz, 1H), 6.94(s, 1H), 6.52(d, J=2.0 Hz, 1H), 6.19(d, J=2.0 Hz, 1H), 3.88(s, 3H), 3.85(s, 3H).

EXAMPLE 28
3',5,7-trihydroxy-4'-methoxy flavone

3',7-dibenzyloxy-4',5-dimethoxy flavone was obtained by the same process of the steps 3) and 4) of the Example 1 using 4-benzyloxy-6-methoxy-2-hydroxy acetophenone as a starting material, and therefrom 3',5,7-trihydroxy-4'-methoxy flavone was obtained by the process of the following step 3).

1) Preparation of 3',4-dibenzyloxy-2-hydroxy-4',6-dimethoxy chalcone

NMR(CDCl$_3$): 14.28(s, 1H), 7.67(s, 2H), 7.40(m, 10H), 7.22(dd, 1H), 7.12(d, 1H), 6.90(d, J=8.3 Hz, 1H), 6.16(d, J=2.3 Hz, 1H), 6.01(d,J=2.3 Hz, 1H), 5.19(s, 2H), 5.06(s, 2H), 3.95(s, 3H), 3.92(s, 3H).

2) Preparation of 3',7-dibenzyloxy-4',5-dimethoxy flavone

NMR(CDCl$_3$): 7.39(m, 12H), 6.96(d, J=8.5 Hz, 1H), 6.58(d, J=2.3 Hz, 1H), 6.53(s, 1H), 6.44(d, J=2.3 Hz, 1H), 5.20(s, 2H), 5.14(s, 2H), 3.94(s, 3H), 3.93(s, 3H).

3) Preparation of 3',5,7-trihydroxy-4'-methoxy flavone

3',7-dibenzyloxy-4',5-dimethyl flavone(400 mg, 0.81 mmol) was dissolved in 12 mL of methylenechloride, and 1M of boron trichloride(2.7 mL) was added hereto at temperature of 0~5° C. Then the reaction mixture was stirred for 40 minutes.

The crystal precipitated in the reaction solution was dissolved in methylenechloride, the organic layer was washed with saturated sodium bicarbonate solution, water and brine, then dried over anhydrous magnesium sulfate, filtered and concentrated to give a yellow crystal of the titled product (184.2 mg, 76%).

NMR(DMSO-d$_6$): 12.93(br s, 1H), 10.88(br s, 1H), 9.46 (br s, 1H), 7.53(dd, 1H), 7.41(d, J=2.1 Hz, 1H), 7.08(d, J=8.7 Hz, 1H), 6.75(s, 1H), 6.46(d, J=2.0 Hz, 1H), 6.18(d, J=2.0 Hz, 1H), 3.85(s, 3H).

2. Preparation of flavanone derivatives

EXAMPLE 29
7-hydroxy-3',4',5-trimethoxy flavanone

1) Preparation of 7-benzyloxy-3',4',5-trimethoxy flavanone

The titled product was synthesized from 4-benzyloxy-3',4',6-trimethoxy-2-hydroxy chalcone as a starting material by the same process of the step 1) of the Example 24.

NMR(CDCl$_3$): 7.39(m, 5H), 6.93(m, 3H), 6.21(d, J=2.2 Hz, 1H), 6.16(d, J=2.2 Hz, 1H), 5.33(dd, 1H), 5.05 (s, 2H), 3.91(s, 3H), 3.89(s, 3H), 3.87(s, 3H), 3.91(s, 3H), 3.89(s, 3H), 3.87(s, 3H), 3.03(dd, 1H), 2.75(dd, 1H).

2) Preparation of 7-hydroxy-3',4',5-trimethoxy flavanone

The titled product was synthesized from 7-benzyloxy-3',4',6-trimethoxy flavanone as a starting material by the same process of the step 5) of the Example 1.

NMR(CDCl$_3$+DMSO-d6): 9,75(br s, 1H), 6.80(m, 3H) 5.97(d, J=2.0 Hz, 1H), 5.92(d, J=1.9 Hz, 1H), 5.18(dd, 1H), 3.75(s, 3H), 3.74(s, 3H), 3.72 (s, 3H), 2.85(dd, 1H), 2.56(dd, 1H).

III. In case that A and B are hydrogen, C, D and E are hydrogen, hydroxy or alkyloxy, respectively

EXAMPLE 30
3',4',5-trimethoxy flavone

The titled product was synthesized from 6-methoxy-2-hydroxy acetophenone as a starting material by the same process of the step 3) and 4) of the Example 1.

1) Preparation of 2-hydroxy-3',4',6-trimethoxy chalcone

NMR(CDCl$_3$): 13.17(s, 1H), 7.75(d, 2H), 7.33(t, 1H), 7.22(dd, 1H), 7.11(d, 1H), 6.88(d, J=8.3 Hz, 1H), 6.60(d, 1H), 6.41(d, 1H), 6.41(d, 1H), 3.93(s, 3H), 3.92 (s, 3H), 3.91(s, 3H).

2) Preparation of 3',4',5-trimethoxy flavone

NMR(CDCl$_3$): 7.55(t, 1H), 7.52(d, 1H), 7.33(d, 1H), 7.11(d, 1H), 6.95(d, 1H), 6.80(d, 1H), 6.65(s, 1H), 3.99(s, 3H), 3.95(s, 3H), 3.94(s, 3H).

IV. In case that A is hydrogen, B is alkyloxy, C, D and E are hydrogen, hydroxy or alkoxy, respectively

EXAMPLE 31
3',4',5,6-tetramethoxy flavone

The titled product was synthesized from 6-methoxy-2-hydroxy acetophenone as a starting material by the same process of the steps 1),2),3) and 4) of the Example 1.

1) Preparation of 2,5-dihydroxy-6-methoxy acetophenone

NMR(CDCl$_3$): 11.96(s, 1H), 7.12(d, J=8.9 Hz, 1H), 6.68 (d, J=9.2 Hz, 1H), 5.10(s, 1H), 3.82(s, 3H), 2.71(s, 3H).

2) Preparation of 2-hydroxy-5,6-dimethoxy acetophenone

NMR(CDCl$_3$): 12.13(s, 1H), 7.10(d, 1H), 6.66(d, 1H), 3.93(s, 3H), 3.82(s, 3H), 2.70(s, 3H).

3) Preparation of 2-hydroxy-3',4',5,6-tetramethoxy chalcone

NMR(CDCl$_3$): 11.92(s, 1H), 7.80(d, J=1.3 Hz, 2H), 7.16 (m, 3H), 6.86(d, 1H), 6.72(d, 1H), 3.91(s, 6H), 3.85(s, 3H), 3.84(s, 3H).

4) Preparation of 3',4',5,6-tetramethoxy flavone

NMR(CDCl$_3$): 7.51(dd J=8.5, 2.1 Hz, 1H), 7.33(d, J=2.1 Hz, 1H), 7.26(d,2H), 6.95(d, J=8.6 Hz, 1H), 6.59(s, 1H), 3.96(s, 3H), 3.95(s, 3H), 3.94(s, 3H), 3.92(s, 3H).

EXAMPLE 32
5-hydroxy-3',4',6-trimethoxy flavone

The titled product was synthesized from 3',4',5,6-tetramethoxy flavanone as a starting material by the same process of the Example 2.

NMR(CDCl$_3$): 12.80(s, 1H), 7.53(dd, 1H), 7.35(d, 1H), 7.23(d, 1H), 6.96(d, 2H), 6.60(s, 1H), 3.97(s, 3H), 3.95(s, 3H), 3.93(s, 3H).

V. In case that A is alkyloxycarboalkyloxy, B, C, D and E are hydrogen or alkoxy group, respectively

EXAMPLE 33
7-methoxycarbomethyloxy-3',4',5-trimethoxy flavone

The mixture of 7-hydroxy-3',4',5-trimethoxy flavone (100 mg, 0.31 mmol), calcium carbonate (84 mg, 2 equivalents) with methyl bromoacetate (43 µl, 1.5 equivalents) in dimethylformamide was stirred at room temperature for 24 hours, and the solvent was evaporated under reduced pressure. The addition of water to the residue resulted the crystallization. This precipitate was filtered and dried to give the titled product(87.46 mg, 72%).

NMR(CDCl$_3$): 7.48(dd, 1H), 7.29(d, J=2.1 Hz, 1H), 6.95 (d, J=8.5 Hz, 1H), 6.58(s, 1H), 6.47(m, 2H), 4.72(s, 2H), 3.95(s, 6H), 3.94(s, 3H), 3.84(s, 3H). VI. In case that A is carboxyalkyloxy, B, C, D and E ar hydrogen, hydroxy or alkyloxy, respectively

EXAMPLE 34
7-carboxymethyloxy-3',4',5,6-tetramethoxy flavone

1) Preparation of 7-t-butyloxycarbomethyloxy-3',4',5,6-tetramethoxy flavone

To a solution of 7-hydroxy-3',4',5,6-tetramethoxy flavone (2.12 g, 5.92 mmol) in 19.7 mL of dimethylformamide was added calcium carbonate (1.64 g, 2 equivalents) and t-butyl bromoacetate (1.05 mL, 1.2 equivalents). The mixture was stirred for 24 hours, to which water was added, then the product was extracted with chloroform twice. The organic layer was dried over anhydrous magnesium sulfate and the solvent was removed under reduced pressure. The residue was column chromatographed to afford the titled product (2.77 g, 99%).

NMR(CDCl$_3$): 7.45(dd, J=8.5, 2.0 Hz, 1H), 7.28(d, J=2.0 Hz, 1H), 6.94(d, J=8.5 Hz, 1H), 6.66(s, 1H), 6.55(s, 1H), 4.66(s, 2H), 3.99(s, 3H) 3.95(s, 6H), 3.93(s, 3H), 1.49(s, 9H).

2) Preparation of 7-carboxymethyloxy-3',4',5,6-tetramethoxy flavone

After 7-t-butyloxycarbomethyloxy-3',4',5,6-tetramethoxy flavone(2.769 g, 5.86 mmol) was dissolved in benzene, and 1.1 g of p-toluenesulfonic acid monohydrate was added hereto, the reaction mixture was refluxed for 3 hours. The resulting precipitate was filtered, washed with benzene and water, then dried to obtain 1.89 g of the titled product (78%).

NMR(DMSO-d$_6$): 13.3(br s, 1H), 7.65(dd, 1H), 7.53(d, 1H), 7.20(s, 1H), 7.10(d, 1H), 6.80(s, 1H), 4.93(s, 2H), 3.88(s, 3H), 3.84(s, 1H) 3.81(s, 6H).

EXAMPLE 35
7-carboxymethyloxy-5-hydroxy-3',4',6-trimethoxy flavone

The titled product was synthesized from 5,7-dihydroxy-3',4',6-trimethoxy flavone as a starting material by the same process of the Example 34.

NMR(DMSO-d$_6$): 12.90(br s,1H), 7.72(dd, J=8.5, 1.9 Hz, 1H), 7.58(d, J=1.9 Hz, 1H), 7.13(d, J=8.6 Hz, 1H), 7.04(s, 1H), 6.95(s, 1H), 4.91(s, 2H), 3.88(s, 3H), 3.85(s, 3H), 3.77(s, 3H).

EXAMPLE 36
7-carboxymethyloxy-3',4',6-trimethoxy flavone

The titled product was synthesized from 7-hydroxy-3',4',6-trimethoxy flavone as a starting material by the same process of the Example 34.

NMR(DMSO-d$_6$): 13.05(br s,1H), 7.68(dd, J=8.6, 2.1 Hz, 1H), 7.56(d, J=2.0 Hz, 1H), 7.39(s, 1H), 7.34(s, 1H), 7.11(d, J=8.6 Hz, 1H), 6.96(s, 1H), 4.90(s, 2H), 3.88(s, 6H), 3.84(s, 3H).

EXAMPLE 37
7-carboxymethyloxy-5-hydroxy-3',4',6-trimethoxy flavanone

The titled compound was synthesized from 5,7-dihydroxy-3',4',6-trimethoxy flavanone as a starting material by the same process of the Example 34.

NMR(CDCl$_3$: 11.91(s, 1H), 6.95(m, 3H), 6.01(s, 1H), 5.33(dd, 1H), 4.72(s, 2H), 3.90(s, 3H), 3.88(s, 3H), 3.87(s, 3H), 3.05(dd, J=13.1 Hz, 1H), 2.78(dd, J=3.1 Hz, 1H).

EXAMPLE 38
7-carboxymethyloxy-3',4',5-trimethoxy flavone

The titled product was synthesized from 7-hydroxy-3',4',6-trimethoxy flavone as a starting material by the same process of the Example 34.

NMR(DMSO-d$_6$): 13.5(br s, 1H), 7.62(dd, 1H), 7.50(d, 1H), 7.09(d, J=8.5 Hz, 1H), 6.83(d, J=2.1 Hz, 1H), 6.74(s, 1H), 6.52(d, J=2.1 Hz, 1H), 4.85(s, 2H), 3.87(s, 3H), 3.83(s, 6H).

EXAMPLE 39
7-carboxymethyloxy-5-hydroxy-6-methoxy-4'-thiomethy flavone

The titled product was synthesized from 5,7-dihydroxy-6-methoxy-4'-thiomethyl flavone as a starting material by the same process of the Example 34.

NMR(CDCl$_3$+DMSO-d$_6$): 12.63(br s, 1H), 7.68(d, 2H), 7.23(d, 2H), 6.51(s, 1H), 6.37(s, 1H), 4.85(s, 2H), 3.83(s, 3H), 2.43 (s, 3H).

EXAMPLE 40
7-carboxymethyloxy-6-n-pentyloxy flavanone

The titled product was synthesized from 7-hydroxy-6-n-pentyloxy flavanone as a starting material by the same process of the Example 34.

NMR(CDCl$_3$): 7.4(m, 6H), 6.48(s, 1H), 5.42(dd, J=13.2, 3.3 Hz, 1H), 4.72(s, 2H), 4.01(t, J=6.8 Hz, 2H), 3.05(dd, J=13.1 Hz, 1H), 2.82(dd, J=3.3 Hz, 1H), 1.82(m, 2H), 1.41(m, 4H), 0.91(t, 3H).

EXAMPLE 41
7-carboxymethyloxy-6-n-pentyloxy flavone

The titled product was synthesized from 7-hydroxy-6-n-pentyloxy flavone as a starting material by the same process of the Example 34.

NMR(DMSO-d$_6$): 8.1(m, 2H), 7.6(m, 3H), 7.38(s, 1H), 7.33(s, 1H), 6.96(s, 1H), 4.92(s, 2H), 4.07(t, J=6.4 Hz, 2H), 3.33(br s, 1H), 1.77(m, 2H), 1.40(m, 4H), 0.90(t, J=6.9 Hz, 3H).

EXAMPLE 42
7-carboxymethyloxy-3',4'-dimethoxy-6-n-pentyloxy flavone

The titled product was synthesized from 7-hydroxy-3',4'-dimethoxy-6-n-pentyloxy flavone as a starting material by the same process of the Example 34.

NMR(DMSO-d$_6$): 13.13(br s, 1H), 7.66(dd, 1H), 7.56(d, 1H), 7.36(s, 1H), 7.30(s, 1H), 7.10(d, J=8.7 Hz, 1H), 6.93 (s,

1H), 4.90(s, 2H), 4.05(t, J=6.4 Hz, 2H), 3.88(s, 3H), 3.84(s, 3H), 1.76(m, 2H), 1.40(m, 4H), 0.90(t, J=6.9 Hz, 3H).

EXAMPLE 43
7-carboxymethyloxy-5-hydroxy-6-methoxy flavone

The titled product was synthesized from 5,7-dihydroxy-6-methoxy flavone as a starting material by the same process of the Example 34.

NMR(DMSO-$d_6$); 12.77(br s, 1H), 8.10(m, 2H), 7,58(m, 3H), 7.04(s, 1H), 6.96(s, 1H), 4.92(s, 2H), 3.78(s, 3H).

EXAMPLE 44
7-carboxymethyloxy-5-hydroxy-6-ethoxy-3',4'-dimethoxy flavone

The titled product was synthesized from 5,7-dihydroxy-6-ethoxy-3',4'-dimethoxy flavone as a starting material by the same process of the Example 34.

NMR(DMSO-$d_6$): 12.86(br s, 1H), 7.72(dd, 1H), 7.58(d, J=1.8 Hz, 1H), 7.13(d, J=8.5 Hz, 1H), 7.03(s, 1H), 6.93(s, 1H), 4.90(s, 2H), 4.03(q, J=6.93 Hz, 1H), 4.90(s, 2H), 4.03(q, J=6.9 Hz, 2H), 3.88(s, 3H), 3.85(s, 3H), 1.27(t, J=7.0 Hz, 3H).

EXAMPLE 45
7-carboxymethyloxy-5-hydroxy-4',6-dimethoxy flavone

The titled product was synthesized from 5,7-dihydroxy-4',6-dimethoxy flavone as a starting material by the same process of the Example 34.

NMR(DMSO-$d_6$): 12.85(br s, 1H), 8.06(d, J=8.9 Hz, 2H), 7.11(d, J=8.9 Hz, 2H), 6.94(s, 1H), 6.93(s, 1H), 4.91(s, 2H), 3.86(s, 3H), 3.77(s, 3H).

EXAMPLE 46
7-carboxymethyloxy-5-hydroxy-6-n-butyloxy-3',4'-dimethoxy flavone The titled compound was synthesized from 5,7-dihydroxy-6-n-butyloxy-3',4'-dimethoxy flavone as a starting material by the same process of the Example 34.

NMR(DMSO-d6): 12.88(s, 1H), 7.72(dd, 1H), 7.59(d, 1H), 7.13(d, J=8.6 Hz, 1H), 7.03(s, 1H), 6.93(s, 1H), 4.88(s, 2H), 3.97(t, J=6.1 Hz, 2H), 3.88(s, 3H), 3.85(s, 3H), 1.65(m, 2H), 1.45(m, 2H), 0.91(t, J=7.2 Hz, 3H).

EXAMPLE 47
7-carboxymethyloxy-5-hydroxy-6-n-propyloxy-3',4'-dimethoxy flavone The titled compound was synthesized from 5,7-dihydroxy-6-n-propyloxy-3',4'-dimethoxy flavone as a starting material by the same process of the Example 34.

NMR(DMSO-$d_6$): 2.88(s, 1H), 7.72(dd, 1H), 7.59(d, 1H), 7.13(d, J=8.6 Hz, 1H), 7.03(s, 1H), 6.93(s, 1H), 4.89(s, 2H), 3.93(t, J=6.4 Hz, 2H), 0.97(t, J=7.4 Hz, 3H).

EXAMPLE 48
7-carboxymethyloxy-5-hydroxy-3',4'-dimethoxy flavone

The titled compound was synthesized from 5,7-dihydroxy-3',4'-dimethoxy flavone as a starting material by the same process of the Example 34.

NMR(DMSO-$d_6$): 12.91(s, 1H), 7,72(dd, 1H), 7.58(d, J=1.7 Hz, 1H), 7.13(d, J=8.6 Hz, 1H), 7.04(s, 1H), 6.82(d, J=2.0 Hz, 1H), 6.37(d, J=2.2 Hz, 1H), 4.84(s, 2H), 3.88(s, 3H), 3.85(s, 3H).

EXAMPLE 49
5-benzyloxy-7-carboxymethyloxy-3',4'-dimethoxy flavone

1) Preparation of 5-benzyloxy-7-t-butyloxycarbomethyloxy-3',4'-dimethoxy flavone The mixture of 7-t-butyloxycarbomethyloxy-5-hydroxy-3',4'-dimethoxy flavone (60 mg, 0.14 mmol), potassium carbonate (39 mg, 2 equivalents) and benzylbromide (25 µl, 1.5 equivalents) in dimethylformamide were heated to reflux.

After the reaction was completed, excess water was added to the mixture to precipitate the desired product, then filtered, washed with water and hexane, and dried to furnish 59 mg of the titled product (81%).

NMR(CDCl$_3$): 7.45(m, 7H), 6.95(d, J=8.5 Hz, 1H), 6.57 (s, 1H), 6.48(s, 2H), 5.23(s, 2H) 4.55(s, 2H), 3.95(s, 3H), 3.93(s, 3H), 1.49(s, 9H).

2) 5-benzyloxy-7-carboxymethyloxy-3',4'-dimethoxy flavone

The titled compound was synthesized from 5-benzyloxy-7-t-butyloxycarbomethyloxy-3',4'-dimethoxy flavone as a starting material by the same process of the step 2 of the Example 34.

NMR(DMSO-$d_6$): 7.20(m, 11H), 5.23(s, 2H), 4.83(s, 2H), 3.88(s, 3H), 3.84(s, 3H).

EXAMPLE 50
5-n-butyloxy-7-carboxymethyloxy-3',4'-dimethoxy flavone

The titled compound was synthesized from 7-t-butyloxycarbomethyloxy-5-hydroxy-3',4'-dimethoxyflavone as a starting material by the same process of the Example 49.

1) Preparation of 5-n-butyloxy-7-t-butyloxycarbomethyloxy-3',4'-dimethoxy flavone NMR(CDCl$_3$); 7.46(dd,1H), 7.29(d, J=2.1 Hz, 1H), 6.94 (d, J=8.5 Hz, 1H), 6.52(s, 1H), 6.45(d, J=2.3 Hz, 1H), 6.43(d, J=2.4 Hz, 1H), 4.58(s, 2H), 4.06(t, J=6.7 Hz, 1H), 3.95(s, 3H), 3.93(s, 3H), 1.90(m, 2H), 1.53(m, 2H), 1.50(s, 9H), 0.98(t, J=7.3 Hz, 3H).

2) Preparation of 5-n-butyloxy-7-carboxymethyloxy-3',4'-dimethoxy flavone

NMR(DMSO-$d_6$): 7.62(dd, 1H), 7.51(d, 1H), 7.10(d, 1H), 6.81(d, 1H), 6.68(s, 1H), 6.52(d, 1H), 4.84(s, 2H), 4.03(t, 2H), 3.87(s, 3H), 3.84(s, 3H), 1.73(m, 2H), 1.52(m, 2H), 0.94(t, J=7.2 Hz, 3H).

EXAMPLE 51
7-carbomethyloxy-5-cyclopentyloxy-3',4'-dimethoxy flavone

The titled compound was synthesized from 7-t-butyloxycarbomethyloxy-5-hydroxy-3',4'-dimethoxy flavone as a starting material by the same process of the Example 49.

1) Preparation of 7-t-butylcarbomethyloxy-5-cyclopentyloxy-3',4'-dimethoxy flavone NMR(CDCl$_3$); 7.45(dd, 1H), 7.28(d, 1H), 6.94(d, J=8.5 Hz, 1H), 6.49(s, 1H), 6.43(d, J=2.2 Hz, 1H), 6.40(d, J=2.2 Hz, 1H), 4.80(m, 1H), 4.57(s, 2H), 3.95(s, 3H), 3.9(s, 3H), 1.96(m, 8H), 1.60(m, 8H), 1.50(s, 9H).

2) Preparation of 7-carboxymethyloxy-5-cyclopentyloxy-3',4'-dimethoxy flavone

NMR(DMSO-$d_6$): 7.62(dd, 1H), 7.50(d, J=2.0 Hz, 1H), 7.10(d, J=8.6 Hz, 1H), 6.80(d, J=2.2 Hz, 1H), 6.66(s, 1H), 6.46(d, J=2.1 Hz, 1H), 4.90(m, 1H), 4.84(s, 2H), 3.88(s, 3H), 3.84(s, 3H), 1.7(m, 8H).

VII. In case that A is N-alkylamidoalkyloxy, B, C, D and E are hydrogen or alkyloxy, respectively

EXAMPLE 52
7-(N-methylamidomethyloxy)-3',4',5-trimethoxy flavone

To a solution of 7-carboxymethyloxy-3',4',5-trimethoxy flavone (154 mg, 0.4 mmol) in 7 mL of dimethylformamide were added hydroxybenzotriazole (74 mg, 1.37 equivalents) and dicyclohexylcarbodiimide (113 mg, 1.37 equivalents) successively at room temperature. The reaction mixture became clear and was suspended again. After 3 hour stirring the methylamineifiHCl (45 mg, 1.66 equivalents) and triethylamine (92 µl, 1.65 equivalents) were successively added at room temperature. After the reaction mixture was stirred for 24 hours, the precipitate was removed by filtration through celite pad and the solvent was removed under reduced pressure. By silica gel chromatography of the residue, the titled product was obtained (86 mg, 54%).

NMR(CDCl$_3$): 7.48(dd, 1H), 7.30(d, J=2.1 Hz, 1H), 6.95 (d, J=8.6 Hz, 1H), 6.60(s,1H), 6.55(d, J=2.3 Hz, 1H), 6.41(d, J=2.3 Hz, 1H), 4.59(s, 2H), 3.96(s,6H), 3.94(s, 3H), 2.93(d, J=4.9 Hz, 3H), 1.23(br s, 1H).

EXAMPLE 53

7-(N-hydroxy-N-methylamidomethyloxy)-3',4',5-trimethoxy flavone 7-carboxymethyloxy-3',4',5-trimethoxyflavone (314 mg, 0.81 mmol) was dissolved in dimethylformamide (14 mL), hereto was added hydroxybenzotriazole (131 mg, 1.2 equivalents) and 1-(3-dimethylaminopropyl)-3-ethyl carbodiimideinHCl (186 mg, 1.2 equivalents). After stirring for 4 hours, N-methylhydroxylamine hydrochloride (81 mg, 1.2 equivalents) and triethylamine (147 mL, 1.3 equivalents) were added. After the mixture was stirred for 24 hours, solvent was removed under reduced pressure and the residue was diluted with chloroform and washed successively with dilute hydrochloric acid, saturated sodium bicarbonate solution and water. Then, the solvent was removed under reduced pressure and then precipitate was crystallized out. By filtering and drying the crystal, the titled product was obtained (141.6 mg, 42%).

NMR(CDCl$_3$+DMSO-d$_6$): 9.41(s,1H), 7.18(dd, J=8.5, 2.1 Hz, 1H), 7.01(d, J=2.0 Hz, 1H), 6.65(d, J=8.5 Hz, 1H), 6.24(d, J=2.2 Hz, 1H), 6.22(s,1H), 6.18(d, J=2.2 Hz, 1H), 4.66(s,2H), 3.63(s,3H), 3.60(s,6H), 2.95(s,3H).

VIII. In case that A is hydroxyalkyloxy, B, C, D and E are hydrogen or alkyloxy, respectively

EXAMPLE 54

7-hydroxyethyloxy-3',4',5-trimethoxy flavone 7-hydroxy-3',4',5-trimethoxy flavone (200 mg, 0.61 mmol) was dissolved in dimethylformamide and hereto was added potassium carbonate (253 mg, 3 equivalents) and 2-bromoethanol (65 µl, 1.5 equivalents). After the reaction mixture was refluxed for 3~4 hours, the solvent was removed under reduced pressure and the residue was diluted with chloroform and washed with water. The organic layer was dried over anhydrous magnesium sulfate, the solvent was removed under reduced pressure and the residue was column-chromatograped to give 125 mg of the product (55%).

NMR(CDCl$_3$): 7.48(dd, J=8.3, 1.9 Hz, 1H), 7.30(d, J=1.8 Hz,1H), 6.94(d, J=8.5 Hz, 1H), 6.58(s, 1H), 6.55(d, J=2.1 Hz, 1H), 6.40(d, J=2.0 Hz, 1H), 4.19(t, J=3.8 Hz, 1H), 4.02(m, 2H), 3.95(s, 6H), 3.93(s, 3H), 2.02(br s, 1H).

EXAMPLE 55

7-hydroxyethyloxy-3',4',5,6-tetramethoxy flavone

The titled product was obtained by the same process of the Example 54.

NMR(CDCl$_3$); 7.48(dd, 1H), 7.30(d, J=2.1 Hz,1H), 6.95 (d, J=8.6 Hz, 1H), 6.81(s, 1H), 6.57(s, 1H), 4.23(t, J=4.2 Hz, 1H), 4.04(m, 2H), 3.98(s, 3H), 3.96(s, 3H), 3.94(s, 3H), 3.91(s, 3H), 2.21(t, 1H).

The molecular structure of the compounds of the formula (I) was identified by measuring Infrared spectroscopy, Ultra-visible spectroscopy, Nuclear magnetic resonance (NMR) spectroscopy, Mass spectroscopy.

In case that the compounds of the formula(I) contain carboxy group, they may exist in the form of free acid or their salt. The salts of the compounds of the formula(I) can be prepared by adding bases to the free acid, wherein the salts should be pharmaceutically acceptable salts. The preferable salts of the present invention are sodium salts, potassium salts, and so on.

The compounds of the formula(I) can be administered orally or non-orally as general types of medicine.

Substantially, the compounds can be administered orally or non-orally and in all the possible dosage forms. When the compounds are prepared for medicine, diluents generally used such as filler, binding agent, damping agent, dissolving agent, and surfactant can be used.

Solid pharmaceutical preparations for oral administration contain tablet, pill, powder, granule and capsule. These solid pharmaceutical preparations are prepared from the compound or mixture of at least one of the compounds along with at least one of diluents such as starch, calcium carbonate, sucrose or lactose, and gelatin. In addition to diluents, lubricating agents such as magnesium stearate talc are used.

Liquid preparations for oral administration contain suspension, solution, emulsion or syrup and they contain damping agent, sweetener, perfume or preserving agent in addition to simple diluents such as water or liquid paraffin.

Preparations for non-oral administration contain sterilized aqueous solutions, non-aqueous solution, suspension, emulsion, lyophilization and suppository. Vegetable oils such as propylene glycol, polyethylene glycol and olive oil or injectable esthers such as ethylolate can be used for non-aqueous solution or suspension. The basement for suppository contain witepsol, macrogol, tween 61, cacao, laurine, glycerogelatin, etc.

The effective amount of the compounds of the formula(I) is 0.1~50 mg/kg, preferably 0.1~30 mg/kg. The compounds of the formula(I) may be administered 1~3 times a day.

We performed experiments as following, by using acute gastritis model induced with ethanolic-hydrochloric acid and by using inflammatory bowel disease model induced with trinitrobenzene sulfonic acid, to confirm that the compounds of the formula(I) have excellent biological effects on healing of inflammatory bowel disease and protection of gastrointestinal tracts.

EXPERIMENT 1

Effect on the Gastritis Model Induced with Ethanolic-HCl.

SD male rat(250–350 g) was fasted for 24 hours. The compound was orally administered in suspension of 5% HPMC, and after 1 hour 1.5 mL of 150 mM HCl-80% ethanol was orally administered. After 1 hour the rat was sacrifieced and the stomach was extracted and the ulcer index was measured. The ulcer index was shown by the area of hemorrhage lesion(Mizui, T, et al., Jpn. J. Pharmacol. 1983, 33: 939).

TABLE 1

Effect on the gastric mucosal damage induced by ethanolic HCl in rats.

| Compounds | Dose (mg/kg.p.o.) | inhibition (%) |
|---|---|---|
| 5,7-dihydroxy-3',4',6-trimethoxy flavone | 0.3 | 58 |
| | 1 | 64 |
| | 3 | 80 |
| 5,7-dihydroxy-3',4',6-trimethoxy flavanone | 0.3 | 5 |
| | 1 | 49 |
| | 3 | 56 |
| 5-hydroxy-3',4',6-trimethoxy flavone | 0.3 | 38 |
| | 1 | 42 |
| | 3 | 64 |
| 7-hydroxy-3',4'5-trimethoxy flavanone | 0.3 | 30 |
| | 1 | 57 |
| | 3 | 76 |
| 7-carboxymethyloxy-3',4',5.6-tetramethoxy flavone | 0.3 | 54 |
| | 1 | 77 |
| | 3 | 84 |
| 7-carboxymethyloxy-5-hydroxy-3',4',6-trimethoxy flavone | 0.3 | 16 |
| | 1 | 77 |
| | 3 | 56 |
| 7-carboxymethyloxy-3',4',6-trimethoxy flavone | 0.3 | 30 |
| | 1 | 31 |
| | 3 | 39 |
| 7-carboxymethyloxy-5-hydroxy-3',4',6-trimethoxy flavanone | 0.3 | 0 |
| | 1 | 18 |
| | 3 | 50 |
| 7-carboxymethyloxy-3',4',5-trimethoxy flavone | 0.3 | 58 |
| | 1 | 68 |
| | 3 | 85 |
| 7-carboxymethyloxy-5-hydroxy-6-butyloxy-3',4'-dimethoxy flavone | 0.1 | 43 |
| | 1 | 61 |
| | 10 | 63 |
| 7-hydroxyethyloxy-3',4',5-trimethoxy flavone | 0.3 | 0 |
| | 1 | 34 |
| | 3 | 47 |
| 7-hydroxyethyloxy-3',4',5,6-tetramethoxy flavone | 0.3 | 43 |
| | 1 | 50 |
| | 3 | 51 |
| 7-methylamidomethyloxy-3',4',5-trimethoxy flavone | 0.3 | 43 |
| | 1 | 47 |
| | 3 | 45 |
| Rebamipide | 3 | 22 |
| | 10 | 30 |
| | 30 | 47 |

* Rebamipide : 2-(4-chlorobenzoylamino)-3-(2-(LH)-quinolinone-4-yl)propanoic acid. Mucosta ®

Table 1 shows that the compounds have significantly potent activity at the dose of 0.3~3 mg, and have 10~100 times more prevention against the damage of gastric mucosa than Rebamipide which is known as the gastric mucous membrane protecting agent.

EXPERIMENT 2

Measurement of Gastric Mucus

The compound was orally administered into SD male rat (200~250 g). After 1 hour the stomach was extracted. The extracted stomach was immediately washed with 10 mL of cold 0.25M sucrose solution. The gastric mucosa was dyed with 0.1% alcian blue solution for 2 hours. After dyeing, the gastric mucosa was washed with 0.25M sucrose solution twice for 15 minutes and for 45 minutes. The dyed gastric mucosa was treated with 10 mL of 30% dioctyl sodium sulfosuccinate solution for 2 hours to extract dyed mucus completely and optical density of aqueous phase was measured spectrophotometrically at 655 nm. The amount of mucus in the gastric mucosa was shown as the amount of alcian blue after calibration (Kitagawa, H., et al., Drug Res. 1986, 36: 1240–1244).

TABLE 2

Effect on the gastric mucus secretion

| | % Control | | | | |
|---|---|---|---|---|---|
| Compounds | 0.3 mg/kg | 3 mg/kg | 10 mg/kg | 30 mg/kg | 100 mg/kg |
| 5,7-dihydroxy-3',4',6-trimethoxy flavone | 132.2 | 130.7 | | 116.8 | |

TABLE 2-continued

Effect on the gastric mucus secretion

| | % Control | | | | |
|---|---|---|---|---|---|
| Compounds | 0.3 mg/kg | 3 mg/kg | 10 mg/kg | 30 mg/kg | 100 mg/kg |
| 7-carboxymethyloxy-3',4',5,6-tetramethoxy flavone | 120 | 130 | | 139 | |
| 7-carboxymethyloxy-3',4',5-trimethoxy flavone | 126.5 | 122.8 | | 117.9 | |
| Rebamipide | | | 128 | | 136 |

In order to know the mechanism of antiulcerative effect of the compounds, the secreted amount of gastric mucus was measured. The compounds of the present invention promoted release of the gastric mucus as shown on the table 2.

EXPERIMENT 3

Measurement of luminol-dependent chemiluminescence of neutrophil induced by FMLP.

20 mL of 12% sodium caseinate-0.9% saline was administered intraperitoneally (Newsby, A. C., Biochem. J., 1980, 186: 907,. After 20 hours, the intraperitoneal exudate was extracted under ether anesthesia. The exudate was centrifuged, and erythrocytes were removed by hypotonic lysis, and then neutrophil was washed. Neutrophil was ascertained by Wright's dyeing method, and viability was measured by Trypan blue exclusion test. Chemiluminescence was measured by Topcount (Packard Co.). The suspension of 1.5×106 of granulocytes, 1 $\mu$M of FMLP, 0.07 mM of luminol and the compound in HBSS was used (Dahlgren, C., et al., Infect. Immun., 1985 47: 326–328).

TABLE 3

Effect on luminol-dependent chemiluminescence of neutrophils induced by FMLP

| Compounds | $IC_{50}(\mu g/mL)$ |
|---|---|
| 5,7-dihydroxy-3',4',6-trimethoxy flavone | 0.463 |
| 7-carboxymethyloxy-3',4',5,6-tetramethoxy flavone | 1.57 |
| 7-carboxymethyloxy-5-hydroxy-3',4',6-trimethoxy flavone | 1.73 |
| 7-carboxymethyloxy-5-hydroxy-3',4',6-trimethoxy flavanone | 1.79 |
| 7-methyloxycarbomethyloxy-3',4',5-trimethoxy flavone | 0.95 |
| 7-hydroxyethyloxy-3',4',5,6-tetramethoxy flavone | 0.13 |
| Rebamipide | 92.1 |

**$IC_{50}(\mu g/mL)$: Concentration of the compound at inhibiting chemiluminescence generated by neutrophil activation to 50%

The effect of the compounds on chemiluminescence of neutrophil of the compound was observed in order to clarify the antiulcerative mechanism. $IC_{50}$ of Rebamipide, which was known as hydroxy radical scavenger, was 92 $\mu$g/mL and $IC_{50}$ of the compounds of the present invention were 0.4¡1.8 $\mu$g/mL, as shown in the table 3. The compounds of the invention are 50~700 times more potent than Rebamipide. The compounds of the invention inhibit the generation of active oxygens from neutrophils or remove the generated active oxygens. These antioxidant activity of compounds of invention may defense the gastric mucosa from its damages by the active oxygens.

EXPERIMENT 4

Measurment of Cyclooxygenase Actvity

After addition of the compound to cultured HUVEC, the HUVEC was incubated at 37° C., for 30 minutes, then arachidonic acid (final concentration: 30 pM) was added, and the HUVEC was additionally incubated at 37° C. for 15 minutes. The culture medium was taken, and the activity of cyclooxygenase for 6-Keto-$PGF_1\alpha$ or $PGE_2$ was measured by radioimmunoassay (Mitchell, J. A., et al., Pro. Natl. Acad. Sci. USA 1994, 90: 11693–11697).

TABLE 4

Effect of compounds on cyclooxygenase activity ($PGF_1\alpha$ synthesis)

| Compounds | $SC_{200}(\mu g/mL)$ |
|---|---|
| 5,7-dihydroxy-3',4',6-trimethoxy flavone | 3.4 |
| 7-carboxymethyloxy-3',4',5,6-tetramethoxy flavone | 11.09 |
| 5,7-dihydroxy-3',4',6-trimethoxy flavanone | 34.6 |
| 7-carboxymethyloxy-5-hydroxy-3',4',6-trimethoxy flavone | 18.41 |
| 7-carboxymethyloxy-3',4',5-trimethoxy flavone | 14.35 |
| 7-carboxymethyloxy-5-hydroxy-6-butyloxy-3',4'-dimethoxy flavone | 2.41 |
| Rebamipide | |

**$SC_{200}(ug/mL)$ : Concentration at increasing generation of $PGF_{1\alpha}$ to 200%

TABLE 5

Effect of compounds on cyclooxygenase ($PGE_2$ synthesis

| Compounds | $SC_{200}(\mu g/mL)$ |
|---|---|
| 5,7-dihydroxy-3',4',6-trimethoxy flavone | 2.4 |
| 7-carboxymethyloxy-3',4',5,6-tetramethoxy flavone | 15.76 |
| 5,7-dihydroxy-3',4',6-trimethoxy flavanone | 3.9 |
| Rebamipide | — |

**$SC_{200}(\mu g/mL)$ : Concentration at increasing generation of $PGE_2$ to 200%

In order to examine cytoprotective effect of the compounds, the compounds of formula(I) was tested whether it can promote the synthesis of prostaglandin. Results showed that cyclooxygenase, the enzyme for the prostaglandin synthesis, was activated in vitro.

Most of the flavonoids affect the metabolic pathway of arachidonic acid, and these compounds of present invention promoted activation of cyclooxygenase as shown in table 4 and 5. The function of promoting biosynthesis of prostaglandins will increase the release of prostaglandins in the gastric mucosa and will eventually lead to the inhibition of the damage of the gastric mucosa.

EXPERIMENT 5

Measurement of 5-lipooxygenase Activity

Modified Safayhi et al.'s method (Safayhi, H., et al., Biochem. Pharmacol. 1985, 34: 2691) was used to this experiment. Peritoneal neutrophil was separated from the rat which was treated with casein solution. The compound was added to $10^7$ cells ($5\times10^6$ cells/mL, 2 mL) of neutrophil after 2 minutes $Ca^{2+}$-ionophore, A23187 (1 μg/mL) was added and the mixture was incubared at 37° C. for 10 minutes. The reaction mixture was centrifuged and the supermatant was taken up. The amount of $LTB_4$ in the supermatant was measured by radioimmunoassay.

TABLE 6

Effect of compounds on 5-lipoxygenase activity

| Compounds | $IC_{50}$(μg/mL) |
|---|---|
| 5,7-dihydroxy-3',4',6-trimethoxy flavone | 4.5 |
| 7-carboxymethyloxy-3',4',5,6-tetramethoxy flavone | 58.24 |
| 7-carboxymethyloxy-3',4',5-trimethoxy flavone | 13.71 |
| 7-carboxymethyloxy-6-pentyloxy-3',4'-dimethoxy flavone | 1.24 |
| 7-carboxymethyloxy-5-hydroxy-6-butyloxy-3',4'-dimethoxy flavone | 11.71 |
| Rebamipide | — |

Damage of the gastric mucosa can be caused by inflammatory reaction cascade such as adhesion of leukocytes to the vascular endothelium and activation of inflammatory cell, and particularly, gastric ulcer induced by NSAIDs such as 1iidomezhacine is explained with inflammatory reaction induced by the increase of leukotriens in the gastric mucosa. The compounds of the invention is to inhibit the activaty of 5-lipoxygenase, which is leukotrien synthesizing enzyme on the metabolic pathway of arachidonic acid and thus the compound is anticipated to have anti-inflammatory effects.

EXPERIMENT 6

Experiment on the Model of Chronic Gastritis Induced with Acetic Acid

By the method of Takagi et al. (Takagi, et. al., Jpn. J. Pharmacol. 1969, 19: 418), the abdomen of SD male rat was opened under ether anesthesis and 50 μl of 10% acetic acid solution was injected into the inner wall of the gastric pylorus and the abdomen was closed. From the next day of the surgical operation, the compound was orally administered once a day for 21 days. After 21 days, the stomach was extracted under ether anesthesis, dipped in 1% formalin solution and the area of gastric lesion was measured. After measuring the area of gastric lesion, the stomach was treated with 10% formalin for over 24 hours, and the site of gastric lesion was sliced to prepare a specimen. An pathological tissue autopsy was carried out for the prepared specimen.

TABLE 7

Inhibiting effect on the model of chronic gastritis induced with acetic acid

| Compounds | Amount (mg/kg.p.o.) | inhibiting% |
|---|---|---|
| 7-carboxymethyloxy-3',4',5,6-tetramethoxy flavone sodium salt | 0.3 | 10 |
| | 3 | 29 |
| | 10 | 42 |
| 7-carboxymethyloxy-3',4',5-trimethoxy flavone sodium salt | 0.3 | 4 |
| | 3 | 83 |
| | 10 | 80 |
| Rebamipide | 10 | 41 |
| | 100 | 7 |

We confirmed that the compounds show the protective effects against the gastric mucosal lesion in the acute model of gastritis induced with ethanolic HCl. Since human gastrointestinal damages are chronic disease, we tried to confirm whether the compounds will show protective effect on gastric mucosal lesion in the chronic models, too. And we found the compounds of the invention show considerable effects at the ⅓ doses of Rebamipide. That is, the compounds have the protective effect against gastric mucosal damage through their antioxidant activity and antinflammatory activity.

EXPERIMENT 7

Experiment on the Model of Inflammatory Bowl Diseases Induced with TNBS

The modified method of Shibata et al. (Dig. Endosc. 1993, 5: 13) was used. 7 week-aged male SD rats were fasted for a day, and the rats were put under anesthesia and canula (diameter 3 mm) was inserted into the anus to the depth of 8 cm. 25 mg/mL of TNBS (Trinitrobenzene sulfonic acid) dissolved in 50% ethanol solution was injected to each rat and the rats were positioned at feature of tail up for 1 minute. The solution flowing out was removed and the rats were once washed with 1.5 mL of saline solution. After colitis was induced, the compound was administered orally or intracolonically once a day for 13 days. For control, mesalazine (5-amino salicylic acid) was used for oral administration and prednisolone was used for rectal administration. At 14th day of experiment, each group of the rats were put under ether anesthesis, the colon was extracted and the degree of adhesion and extension of the large intestine were measured and their lesion scores were recorded. After 1% formalin solution was injected to the cavity of the extracted colon to inflate, the both ends of it were bonded with each other and it was all-fixed in 1% formalin solution for 2 hours. The all-fixed colon was cut to lengthy direction and washed to remove surrounding fat tissues and connective fissaes. After cecum was removed, the weight of the colon and the rectum was measured, and the area of ulcer lesion, and microscopic lesion were measured to mark scores according to the criterion. And they were fixed in 10% neutral formalin solution, and the tissue examination of lesion site was performed by general method to mark scores according to the criterion.

Clinical symptoms: Daily, we observed clinical symptoms and survival of the animals. And we measured the weight of the animals at the beginning day, third and eighth day of the experiment.

Adhesion degree of the large intestine: We marked scores of the degree of the adhesion of the large intestine according to the criterion, following the methods of Kim at al. (Korean J. Med. 1994, 47: 20), and compared with the average value of each group.

(0: non-adhesion, 1: adhesion exists but easily taken off by gloved hand, 2: more severe adhesion than 1 exists but easily taken off by scissors, 3: very severe adhesion exists, so it is difficult to be taken off by scissors because of possibility of its perforation.)

Degree of thickening and extension of the large intestine: We marked scores of the degree of thickness and extension of the large intestine according to the criterion, following the method of Kim et al., and compared with the average value of each group.

(0: lesion site non-existing, 1: a few degree of lesion, 2: intermediate degree of lesion, 3: severe degree of lesion)

Macroscopic evaluation: We measured the number and the width of the ulcer and lesion area formed in the large intestine, by using modified Wallace's method (Can. J. Physiol. Pharmacol., 1988, 66: 422). We scored the lesion examined with the naked eye and compared the average value of each group. The standards of lesion scores as criterion of the damage of the colon by Wallace's method is as followings.

(0: normal, non-damaged, 1: congestion without ulcer 2: congestion and thickening of intestinal wall without ulcer, 3: an ulcer lesion without thickening of intestinal wall, 4: more than two ulcerous/inflammatory lesion, 5: more than two ulcerous/inflammatory lesion or the length of ulcerous/ inflammatory lesion is more than 1 cm, 6–10: when the length of lesion is over 2 cm, one point increases everytime 1 cm of the length of ulcerous/inflammatory increases, for example, when the ulcer length is 3 cm, the point is 7.)

Microscopic evaluation: We trimmed the colon giving 3 cm interval from the rectum to the cecum, including the site of lesion examined with the naked eye, to make at least 4 specimens per an individual. We did pathological tissue examination on the specimens, and using modified method of Moyama (Ann. Clin. Lab. Sci., 1990, 20: 420), we marked scores of them and accepted the highest score as the score of the individual's. When the lesion can not be examined with the naked eye, we trimmed the other specimen which has the lesion, with 3 cm interval.

TABLE 8

Effect of the compounds when orally administered on TNBS-induad colitis model

| Compounds | Amount (mg/k,p.o.) | lesion scores | adhesion degree | dilation and extention degree |
|---|---|---|---|---|
| 5% HPMC | | 37 | 15 | 1.3 |
| 7-carboxymethyloxy-3',4',5,6-tetramethoxy flavone sodium salt | 1 | 1.3 | 0.5 | 0.3 |
| | 10 | 0.8 | 0.6 | 0.4 |
| mesalazine | 25 | 2.8 | 1.4 | 0.9 |
| | 50 | 2.2 | 1.0 | 1.1 |

TABLE 9

Effects of the compounds whenintracolonically administered on the TNBS-induced colitis model.

| Compounds | Amount (mg/kg, rectally) | lesion scores |
|---|---|---|
| 5% HPMC | | 4.00 |
| 7-carboxymethyloxy-3',4',5,6-tetra- methoxy flavone sodium salt | 0.3 | 2.56 |
| | 3 | 2.60 |
| 7-carboxymethyloxy-3',4',5-tri- methoxy flavone sodium salt | 0.3 | 4.43 |
| | 3 | 0.86 |
| prednisolone | 1 | 0.83 |

The compounds of invention showed the inhibiting effect on the model of inflammatory colitis by oral or rectal administration as shown in the table 8 and 9. These anti-colitic effect might be ascribed to the activity of mucous membrane protection, anti-oxidation and leukotrien synthesis inhibition and furthermore the compounds are more potent than mesalazine broadly used in the market.

We carried out following experiment to find out the acute toxicity of the compounds of the formula(I).

EXPERIMENT 8

Experiment for Acute Toxicity Using Mouse.

Acute toxicity was examined by using ICR mouse. The compounds dissolved in distilled water were administered orally. To the animals, three individuals/group, were given 5 g/kg of 7-carboxymethyloxy-3',4',5,6-tetramethoxy flavone and 7-caroxymethyloxy-3',4',5-trimethoxy flavone, respectively, and all of the animals did not show any particular clinical symptoms and all survived.

Thus, the compounds are proved to be safe materials for oral administration, whose $LD_{50}$ is over 5 g/kg.

Flavone and flavanone derivatives of the formula(I) of the present invention stimulate cylo-oxygenase activity. In arachidonic acid metabolic pathway, cyclooxygenase catayzes synthesis of prosta-glandins such as $PGE_2$ and $PGI_2$, which have gastric mucosa protecting function. The compounds of the present invention also inhibited activation of 5-lipoxygenase and resulted the inhibition of synthesis of leukotriens, which are major inflammatory mediator. They also have activity to inhibit synthesis of active oxygens produced by inflammatory cells which is activated during immune reaction. Thus, the effects of the compounds of the present invention can be summarized as follows.

First, they show excellent effects on gastritis, gastric ulcer, duodenal ulcer, digestive ulcer and chronic ulcer induced with NSAIDs. These diseases are known to be caused by suppression of the prostaglandin synthesis or by active oxygen produced by activated inflammatory cells.

Second, the compounds show good effects on inflammatory colitis, ileitis, local ileitis, granulative colitis, hard wall colitis, ileocolitis, arthritis induced with ulcerative colitis, and uveitis. These diseases are known to be caused by increasing leukotrien synthesis in mucous membrane, or by active oxygen produced by activated inflammatory cells.

What is claimed is:

1. Flavone/flavanone compounds or their pharmaceutically acceptable salts having the following formula(I);

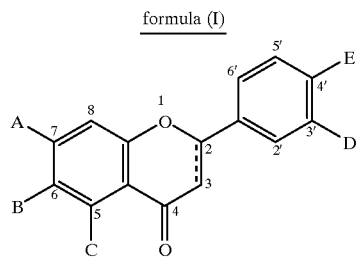

formula (I)

wherein A is selected from a group consisting of alkyloxycarboalkyloxy, carboxyalkyloxy, N-alkylamidoalkyloxy, hydroxyalkyloxy and cycloalkyloxy group, B and C, which are the same or different, are respectively selected from a group consisting of hydrogen, hydroxy, unsubstituted or mono-substituted alkyloxy and cycloalkyloxy group, D and E, which are the same or different, are respectively selected from a group consisting of hydrogen, hydroxy, lower alkyloxy having normal and branched chain with one to six carbon atoms, and the bond between 2-position and 3-position is single or double.

2. Flavone/flavanone compounds or their pharmaceutically acceptable salts according to claim 1, wherein substituent of alkyloxy group is selected from a group consisting of hydroxy, carboxy, alkylester of carboxy, carboxamide, N-mono or dialkyl carboxamide, N-hydroxy carboxamide, N-hydroxy-N-alkyl carboxamide and substituted or unsubstituted benzene ring.

3. Flavone/flavanone compounds or their pharmaceutically acceptable salts according to claim 1, wherein A is alkyloxycarboalkyloxy, B, C, D and E are respectively selected from a group consisting of hydrogen and alkyloxy.

4. Flavone/flavanone compounds or their pharmaceutically acceptable salts according to claim 1, wherein A is carboxyalkyloxy, B, C, D and E are respectively hydrogen, hydroxy and alkyloxy.

5. Flavone/flavanone compounds or their pharmaceutically acceptable salts according to claim 1, wherein A is N-alkylamidoalkyloxy, B, C, D and E are respectively selected from a group consisting of hydrogen and alkyloxy.

6. Flavone/flavanone compounds or their pharmaceutically acceptable salts according to claim 1, wherein A is hydroxyalkyloxy, B, C, D and E are respectively selected from a group consisting of hydrogen and alkyloxy.

7. Flavone/flavanone compounds or their pharmaceutically acceptable salts according to claim 1, wherein the compound is selected from a group of consisting of 7-carboxymethyloxy-3',4',5,6-tetramethoxy flavone, 7-carboxymethyloxy-5-hydroxy-3',4',6-trimethoxy flavone, 7-carboxymethyloxy-5-hydroxy-3',4',6-trimethoxy flavanone, 7-carboxymethyloxy-3',4',5-trimethoxy flavone, 7-carboxymethyloxy-3',4'-dimethoxy-6-n-pentyloxy flavone, 7-carboxymethyloxy-5-hydroxy-6-n-butyloxy-3',4'-dimethoxy flavone, 7-N-methylamidomethyloxy-3',4',5-trimethoxy flavone, 7-(N-hydroxy-N-methylamidomethyloxy)-3',4',5-trimethoxy flavone, 7-hydroxyethyloxy-3',4',5-trimethoxy flavone, and 7-hydroxyethyloxy-3',4',5,6-tetramethoxyflavone.

8. Pharmaceutical composition for preventing or treating damages of mucous membrane of the gastrointestinal tracts or for treating inflammatory bowel disease, which contains flavone/flavanone compounds of the formula(I) of claim 1 or their pharmaceutically acceptable salts, as effective ingredient(s).

9. Process for preparing flavone/flavanone compounds of the formula(I) of claim 1, which comprises the steps of:

1) reacting 2-hydroxyacetophenone appropriately substituted with A, B and C with benzaldehyde appropriately substituted with D and E to obtain chalcone;

2) cylizing the chalcone to make the skeletal structure of flavone or flavanone compounds of the formula(I) of claim 1;

3) deprotecting appropriate protecting group of corresponding substitutent of flavone/flavanone compounds of the formula(I) of claim 1;

4) putting the desired substituent at the deprotected position(s).

* * * * *